United States Patent
Freyne et al.

(10) Patent No.: US 6,403,805 B1
(45) Date of Patent: *Jun. 11, 2002

(54) 1,3-DIHYDRO-1-(PHENYLALKYL)-2H-IMIDAZOL-2-ONE DERIVATVES

(75) Inventors: Eddy Jean Edgard Freyne, Rumst; Gaston Stanislas Marcella Diels, Ravels, both of (BE); José Ignacio Andrés-Gil, Madrid; Francisco Javier Fernández-Gadea, Toledo, both of (ES)

(73) Assignee: Janssen Pharmaceutica N.V., Beerse (BE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/362,007

(22) Filed: Jul. 27, 1999

Related U.S. Application Data

(62) Division of application No. 08/930,296, filed as application No. PCT/EP96/01392 on Mar. 28, 1996, now Pat. No. 5,994,376.

(30) Foreign Application Priority Data

Apr. 6, 1995 (EP) ............................................ 95200868
Oct. 26, 1995 (EP) ............................................ 95202898

(51) Int. Cl.$^7$ ................... C07D 233/32; C07D 233/36; C07D 233/70; C07D 40/06
(52) U.S. Cl. ................... 548/315.4; 514/391; 514/399; 514/400; 514/397; 548/323.5; 548/325.1; 548/325.5
(58) Field of Search ........................ 548/315.4, 323.5, 548/325.1, 325.5; 514/391, 397, 399, 400

(56) References Cited

U.S. PATENT DOCUMENTS 3,184,060 A 5/1965 Akkerman et al. .. 548/323.5 X
5,994,376 A 11/1999 Freyne et al. ................ 514/341

FOREIGN PATENT DOCUMENTS

| WO | WO 9207567 | 5/1992 |
| WO | WO 9412461 | 6/1994 |
| WO | WO 9414742 | 7/1994 |
| WO | WO 94-20446 | 9/1994 |

OTHER PUBLICATIONS

Matoba et al., Chem. Pharm. Bull. Synthesis in the Diazasteroid Group . . . 28 (6), 1810–1813 (1990).
Kano et al., Synthetic Communications, A Synthesis is Fused Heterocyclic Isoquinolines . . . 15 (10), 883–889 (1985).
Chemical Abstracts, vol. 78, 21, abstract No. 136297v, W.L. Matier et al. (May 28, 1973).
Chemical Abstracts, vol. 82, 21 abstract No. 139667j, J.T. Suh (May 26, 1975).
Chemical Abstracts, vol. 70, 7 abstract No. 28525u, G.P. Bettinetti et al. (Feb. 17, 1969).
B. Lesechi et al., European J. of Medicinal Chem.–Chimica Therapeutica vol. 13, 2, 183–192 (1978). (English Abstract).
Chemical Abstracts, vol. 64, 7, abstract No. 9681C, J. Knabe et al. (Mar. 28, 1966).
G. Schwachhofer et al., Bulletin de la Societe Chimique de France, 835–843 (1962).
Chemical Abstracts, vol. 89, 13, abstract No. 109448r, A. Huth et al. (Sep. 25, 1978).
P. F. Kador et al., Journal of Medicinal Chemistry, 20, 7, 891–894 (1977).
DE–C–711, 625 (Oct. 14, 1941), Kindler.
D. Shapiro, Journal of Organic Chemistry vol. 16, 8, 1247–1249 (1951).
Journal of the American Chemical Society, vol. 69, 12, 3150 Jan. 5, 1948). Duschinsky et al.
J. Harley–Mason et al., Journal of the Chemical Society (London), Letchworth GB, 1165–1171 (1954).
Chemical Abstracts, vol. 87, 17, abstract No. 134458k, H.J. Runge et al. (Oct. 24, 1977).
J. D. White et al., Journal of the American Chemical Society, vol. 116, 5, 1831–1838 (May 9, 1994).
R. T. Borchardt et al., Journal of Medicinal Chemistry, 19, 1, 30–37 (Jan. 1976).
Chemical Abstracts, vol. 52, 8, abstract No. 6342B, S. Chiavarelli et al. (Apr. 25, 1958).
Chemical Abstracts, vol. 82, 21, abstract No. 139935v, E. A. Markaryan et al. (May 26, 1975).
H. J. Dyke et al, Exp. Opin. Invest. Drugs, 8(9), 1301–1325 (1999).

Primary Examiner—Floyd D. Higel
(74) Attorney, Agent, or Firm—Mary Appollina

(57) ABSTRACT

The present invention describes compounds useful for treating warm-blooded animals suffering from disease states related to an abnormal enzymatic or catalytic activity of phosphodiesterase IV (PDE IV), and/or disease states related to a physiologically detrimental excess of cytokines, in particular allergic, atopic and inflammatory diseases, said compounds having the formula (I)

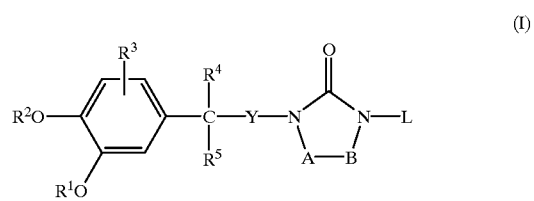

the N-oxide forms, the pharmaceutically acceptable acid or base addition salts and the stereochemically isomeric forms thereof.

16 Claims, No Drawings

1,3-DIHYDRO-1-(PHENYLALKYL)-2H-IMIDAZOL-2-ONE DERIVATVES

CROSS REFERENCE TO RELATED APPLICATIONS

This application is a divisional application of U.S. Ser. No. 08/930,296, filed Sep. 29, 1997, now issued as U.S. Pat. No. 5,994,376 which is a National Stage application under 35 U.S.C. 371 of PCT/EP96/01394 filed Mar. 28, 1996, which claims priority from EP 95.200.868.8, filed Apr. 6, 1995, and EP 95.202.893.3, filed Oct. 26, 1995.

The present invention concerns the use of 1,3-dihydro-1-(phenylalkyl)-2H-imidazol-2-one derivatives for the manufacture of a medicament for treating warm-blooded animals suffering from disease states related to an abnormal enzymatic or catalytic activity of phosphodiesterase IV (PDE IV), and/or disease states related to a physiologically detrimental excess of cytokines, in particular allergic, atopic and inflammatory diseases. The present invention also relates to new compounds having PDE IV and cytokine inhibiting activity, processes for their preparation and compositions comprising said new compounds.

1-[2-(3,4-diethoxyphenyl)ethyl]-1,2-dihydro-2H-imidazol-2-one and a number of (1,3-dihydro- and 1,3,4,5-tetrahydro-)(1-[2-(3,4-dimethoxyphenyl)propyl]- and 1-[2-(3,4-dimethoxyphenyl)ethyl])-2H-imidazol-2-one derivatives are specifically disclosed in U.S. Pat. No. 3,184,460 as therapeutic agents acting on the central nervous system, in particular, as tranquilizers. Synthetic Communications (1985) 15(10), 883–889, discloses a synthetic pathway for the preparation of 1,3,4,5-tetrahydro-1-[2-(3,4-dimethoxy-phenyl)ethyl]-3-phenylmethyl-2H-imidazol-2-one. In the Chemical and Pharmaceutical Bulletin (1980), 28(6), 1810–1813, 1,3,4,5-tetrahydro-1,3-bis[2-(3,4-dimethoxyphenyl)ethyl]-2H-imidazol-2-one and 1,3,4,5-tetrahydro-1-[2-(3,4-dimethoxyphenyl)ethyl]-2H-imidazol-2-one are disclosed as intermediates in the synthesis of a diazasteroid system. WO 94/12461, WO 94/14742 and WO 94/20446 generically describe a number of 1-(phenylalkyl)-2-hydroxy-imidazole derivatives as selective PDE IV inhibitors.

Unexpectedly, particular 1,3-dihydro-1-(phenylalkyl)-2H-imidazol-2-one derivatives show improved PDE IV inhibiting activity over the art compounds. In addition, the compounds of the present invention were found to display cytokine inhibiting activity. In view of these pharmacological properties, the present compounds have therapeutical utility in the treatment of disease states related to an abnormal enzymatic or catalytic activity of PDE IV, or disease related to a physiologically detrimental excess of cytokines, in particular allergic, atopic and inflammatory diseases.

The present invention concerns the use of compounds of formula (I) for the manufacture of a medicament for treating warm-blooded animals suffering from disease states related to an abnormal enzymatic or catalytic activity of phosphodiesterase IV (PDE IV), and/or disease states related to a physiologically detrimental excess of cytokines, in particular allergic, atopic and inflammatory diseases, and compounds having the formula

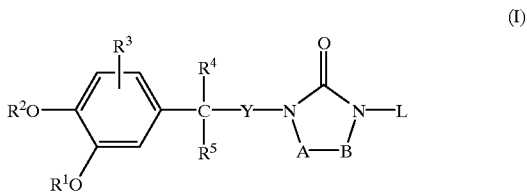

the N-oxide forms the pharmaceutically acceptable acid or base addition salts and the stereochemically isomeric forms thereof, wherein:

$R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

$R^4$ is hydrogen, halo or $C_{1-6}$alkyloxy;

$R^3$ is hydrogen, halo; $C_{1-6}$alkyl; trifluoromethyl; $C_{3-6}$cycloalkyl; carboxyl; $C_{1-4}$alkyloxycarbonyl; $C_{3-6}$cycloalkylaminocarbonyl; aryl; $Het^1$; or $C_{1-6}$alkyl substituted with cyano, amino, hydroxy, $C_{1-4}$alkylcarbonylamino, aryl or $Het^1$; or $R^4$ is a radical of formula:

—O—$R^6$ (a-1); or

—NH—$R^7$ (a-2);

wherein $R^6$ is hydrogen; $C_{1-6}$alkyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$ alkyl)amino, $Het^1$ or aryl;

$R^5$ is hydrogen, halo, hydroxy or $C_{1-6}$alkyl; or $R^4$ and $R^5$ taken together may form a bivalent radical of formula:

—(CH$_2$)$_n$— (b-1);

—CH$_2$—CH$_2$—O—CH$_2$—CH$_2$— (b-2);

—CH$_2$—CH$_2$—N(R$^8$)—CH$_2$—CH$_2$— (b-3); or

—CH$_2$—CH=CH—CH$_2$— (b-4);

wherein n is 2, 3, 4 or 5;

$R^8$ is hydrogen, $C_{1-6}$alkyl, $C_{1-6}$alkylsulfonyl or p-toluenesulfonyl;

Y is a direct bond, halo$C_{1-4}$alkanediyl or $C_{1-4}$alkanediyl;

—A—B— is a bivalent radical of formula:

—CR$^9$=CR$^{10}$— (c-1); or

—CHR$^9$—CHR$^{10}$— (c-2);

wherein each $R^9$ and $R^{10}$ independently is hydrogen or $C_{1-4}$alkyl; and L is hydrogen; $C_{1-6}$alkyl; $C_{1-6}$alkylcarbonyl; $C_{1-6}$alkyloxycarbonyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and Het$^2$; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;

Het$^1$ is pyridinyl; pyridinyl substituted with $C_{1-4}$alkyl; furanyl; furanyl substituted with $C_{1-4}$alkyl; thienyl; thienyl substituted with $C_{1-4}$alkylcarbonylamino; hydroxypyridinyl, hydroxypyridinyl substituted with $C_{1-4}$alkyl or $C_{1-4}$alkoxy-$C_{1-4}$alkyl; imidazolyl; imidazolyl substituted with $C_{1-4}$alkyl; thiazolyl; thiazolyl substituted with $C_{1-4}$alkyl; oxazolyl; oxazolyl substituted with $C_{1-4}$alkyl; isoquinolinyl; isoquinolinyl substituted with $C_{1-4}$alkyl; quinolinonyl, quinolinonyl substituted with $C_{1-4}$alkyl; morpholinyl; piperidinyl; piperidinyl substituted with $C_{1-4}$alkyl, $C_{1-4}$alkyloxycarbonyl or aryl$C_{1-4}$alkyl; piperazinyl; piperazinyl substituted with $C_{1-4}$alkyl, $C_{1-4}$alkyloxycarbonyl or aryl$C_{1-4}$alkyl; and Het$^2$ is morpholinyl; piperidinyl; piperidinyl substituted with $C_{1-4}$alkyl or aryl$C_{1-4}$alkyl; piperazinyl; piperazinyl substituted with $C_{1-4}$alkyl or aryl$C_{1-4}$alkyl; pyridinyl; pyridinyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino.

The present invention also relates to a method of treating warm-blooded animals suffering from disease states related to an abnormal enzymatic or catalytic activity of PDE IV, and/or disease states related to a physiologically detrimental excess of cytokines, in particular allergic, atopic and inflammatory diseases, more in particular asthmatic and atopic diseases, most particular atopic dermatitis. Said method comprises the administration of a therapeutically effective amount of a compound of formula (I) or a N-oxide form, a pharmaceutically acceptable acid or base addition salt or a stereochemically isomeric form thereof in admixture with a pharmaceutical carrier.

Some of the compounds of formula (I) may also exist in their tautomeric forms. Such forms although not explicitly indicated in the above formula are intended to be included within the scope of the present invention.

In $R^1$ and $R^2$, the saturated 5-, 6- and 7-membered heterocycles containing one or two heteroatoms selected from oxygen, sulfur or nitrogen may suitably be selected from heterocycles such as, for example, tetrahydrofuranyl, dioxolanyl, pyrrolidinyl, morpholinyl, piperidinyl, piperazinyl and tetrahydropyranyl. Said heterocyclic radicals are attached to the $C_{1-10}$alkyl radical by any carbon atom or, where appropriate, by a nitrogen atom.

As used herein the term halo is generic to fluoro, chloro, bromo and iodo; the term $C_{1-4}$alkyl is meant to include straight chained or branched saturated hydrocarbons having from 1 to 4 carbon atoms such as, for example, methyl, ethyl, 1-methylethyl, 1,1-di-methylethyl, propyl, 2-methylpropyl and butyl; the term $C_{4-6}$alkyl is meant to include straight chained or branched saturated hydrocarbons having from 4 to 6 carbon atoms such as, for example, 2-methylpropyl, butyl, 2-methylbutyl, pentyl, hexyl and the like; the term $C_{3-6}$alkyl is meant to include $C_{4-6}$-alkyl and the lower homologues thereof having 3 carbon atoms such as, for example, propyl and 1-methylethyl; the term $C_{2-6}$alkyl is meant to include $C_{3-6}$alkyl and the lower homologues thereof having 2 carbon atoms such as, for example, ethyl; the term $C_{1-6}$alkyl is meant to include $C_{2-6}$alkyl and the lower homologue thereof having 1 carbon atom such as, for example, methyl; $C_{1-10}$alkyl is meant to include $C_{1-6}$alkyl and the higher homologues thereof having from 7 to 10 carbon atoms such as, for example, heptyl, octyl, nonyl, decyl, 1-methylhexyl, 2-methylheptyl and the like; the term $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated; the term $C_{3-6}$cycloalkyl is generic to cyclopropyl, cyclobutyl, cyclopentyl and cyclohexyl; the term $C_{3-7}$cycloalkyl is meant to include $C_{3-6}$cycloalkyl and cycloheptyl; the term $C_{1-2}$alkanediyl is meant to include methylene, 1,2-ethanediyl and 1,1-ethanediyl; the term $C_{1-3}$alkanediyl is meant to include $C_{1-2}$alkanediyl and the higher homologues thereof being straight chained and branched saturated bivalent hydrocarbon radicals having 3 carbon atoms, such as, for example, 1,3-propanediyl, 1,2-propanediyl; the term $C_{1-4}$alkanediyl is meant to include $C_{1-3}$-alkanediyl and the higher homologues thereof having 4 carbon atoms such as, for example, 1,4-butanediyl, 2-methyl-1,3-propanediyl and the like.

As used in the foregoing definitions and hereinafter, halo$C_{1-4}$alkanediyl is defined as mono- or polyhalosubstituted $C_{1-4}$alkanediyl, in particular $C_{1-4}$alkanediyl substituted with one or more fluoro atoms.

The pharmaceutically acceptable acid addition salts as mentioned hereinable are meant to comprise the acid addition salt forms which can conveniently be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxy-acetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicyclic, p-aminosalicyclic, pamoic and the like acids. Conversely, said acid addition salt forms can be converted in three free base forms by treatment with an appropriate base.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine N-methyl-D-glucamine, hydrabamine salts, and salts with amino acids such as, for example, arginine lysine and the like.

The term addition salt also comprises the hydrates and solvent addition forms which the compounds of formula (I) are able to form. Examples of such forms are e.g. hydrates, alcoholates and the like.

The N-oxide forms of the compounds of formula (I) are meant to comprise those compounds of formula (I) wherein one or several nitrogen atoms are oxidized to the so-called N-oxide.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration.

Whenever used hereinafter, the term compounds of formula (I) is meant to include also the N-oxide forms, the pharmaceutically acceptable acid or base addition salts and all stereoisomeric forms.

Some of the compounds of formula (I) and some of the intermediates in the present invention may contain an asymmetric carbon atom. Pure stereochemical isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced with the scope of the present invention.

An alternative manner of separating the enantiomeric forms of the compounds of formula (I) and intermediates involves liquid chromatography, in particular liquid chromatography using a chiral stationary phase.

The compounds of formula (I) are deemed novel, provided that the compound is other than:
1,3-dihydro-1-[2-(3,4-dimethoxyphenyl)propyl]-2H-imidazol-2-one;
1,3-dihydro-1-[2-(3,4-dimethoxyphenyl)propyl]-5-methyl-2H-imidazol-2-one;
1-[2-(3,4-dimethoxyphenyl)ethyl]-1,3,4,5-tetrahydro-2H-imidazol-2-one;
1,3-dihydro-1-[2-(3,4-dimethoxyphenyl)ethyl]-2H-imidazol-2-one;
1-[2-(3,4-dimethoxyphenyl)propyl]-1,3,4,5-tetrahydro-2H-imidazol-2-one;
1-[2-(3,4-diethoxyphenyl)ethyl]-1,3-dihydro-2H-imidazol-2-one;
1,3-bis[2-(3,4-dimethoxyphenyl)ethyl]-1,3,4,5-tetrahydro-2H-imidazol-2-one; or
1-[2-(3,4-dimethoxyphenyl)ethyl]-3-phenylmethyl-1,3,4,5-tetrahydro-2H-imidazol-2-one.

Thus, the invention concerns novel compounds having the formula

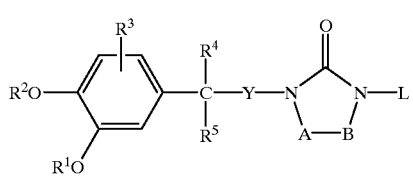

(I')

the N-oxide forms, the pharmaceutically acceptable acid or base addition salts and the stereochemically isomeric forms thereof, wherein:

$R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- 7-membered heterocycle containing one or two heteroatoms selected from oxygen, sulfur or nitrogen;

$R^3$ is hydrogen, halo or $C_{1-6}$alkyloxy;

$R^4$ is hydrogen, halo; $C_{1-6}$alkyl; trifluoromethyl; $C_{3-6}$cycloalkyl; carboxyl; $C_{1-4}$alkyloxycarbonyl; $C_{3-6}$cycloalkylaminocarbonyl; aryl; $Het^1$; or $C_{1-6}$alkyl substituted with cyano, amino, hydroxy, $C_{1-4}$alkylcarbonylamino, aryl or $Het^1$; or $R^4$ is radical of formula:

—O—$R^6$ (a-1); or

—NH—$R^7$ (a-2);

wherein $R^6$ is hydrogen; $C_{1-6}$alkyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^5$ is hydrogen, halo, hydroxy or $C_{1-6}$alkyl; or $R^4$ and $R^5$ taken together may form a bivalent radical of formula:

—$(CH_2)_n$— (b-1);

—$CH_2$—$CH_2$—O—$CH_2$—$CH_2$— (b-2);

—$CH_2$—$CH_2$—N($R^8$)—$CH_2$—$CH_2$— (b-3); or

—$CH_2$—CH=CH—$CH_2$— (b-4);

wherein n is 2, 3, 4 or 5;

$R^8$ is hydrogen, $C_{1-6}$alkyl, $C_{1-6}$alkylsulfonyl or p-toluenesulfonyl;

Y is a direct bond, halo$C_{1-4}$alkanediyl or $C_{1-4}$alkanediyl;

—A—B— is a bivalent radical of formula:

—$CR^9$=$CR^{10}$— (c-1); or

—$CHR^9$—$CHR^{10}$— (c-2);

wherein each $R^9$ and $R^{10}$ independently is hydrogen or $C_{1-4}$alkyl; and L is hydrogen; $C_{1-6}$alkyl; $C_{1-6}$alkylcarbonyl; $C_{1-6}$alkyloxycarbonyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and $Het^2$; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;

$Het^1$ is pyridinyl; pyridinyl substituted with $C_{1-4}$alkyl; furanyl; furanyl substituted with $C_{1-4}$alkyl; thienyl; thienyl substituted with $C_{1-4}$alkylcarbonylamino;

hydroxy-pyridinyl, hydroxypyridinyl substituted with $C_{1-4}$alkyl or $C_{1-4}$alkoxy$C_{1-4}$alkyl; imidazolyl; imidazolyl substituted with $C_{1-4}$alkyl; thiazolyl; thiazolyl substituted with $C_{1-4}$alkyl; oxazolyl; oxazolyl substituted with $C_{1-4}$alkyl; isoquinolinyl; isoquinolinyl substituted with $C_{1-4}$alkyl; quinolinonyl, quinolinonyl substituted with $C_{1-4}$alkyl; morpholinyl; piperidinyl; piperidinyl substituted with $C_{1-4}$alkyl, $C_{1-4}$alkyloxycarbonyl or aryl$C_{1-4}$alkyl; piperazinyl; piperazinyl substituted with $C_{1-4}$alkyl, $C_{1-4}$alkyloxycarbonyl or aryl$C_{1-4}$-alkyl; and $Het^2$ is morpholinyl; piperidinyl; piperidinyl substituted with $C_{1-4}$alkyl or aryl$C_{1-4}$alkyl; piperazinyl; piperazinyl substituted with $C_{1-4}$alkyl or aryl $C_{1-4}$alkyl; pyridinyl; pyridinyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino:

provided that the compound is not:
1,3-dihydro-1-[2-(3,4-dimethoxyphenyl)propyl]-2H-imidazol-2-one;
1,3-dihydro-1-[2-(3,4-dimethoxyphenyl)propyl]-5-methyl-2H-imidazol-2-one;
1-[2-(3,4-dimethoxyphenyl)ethyl]-1,3,4,5-tetrahydro-2H-imidazol-2-one;
1,3-dihydro-1-[2-(3,4-dimethoxyphenyl)ethyl]-2H-imidazol-2-one;
1-[2-(3,4-dimethoxyphenyl)propyl]-1,3,4,5-tetrahydro-2H-imidazol-2-one;
1-[2-(3,4-dimethoxyphenyl)ethyl]-1,3-dihydro-2H-imidazol-2-one;
1,3-bis[2-(3,4-dimethoxyphenyl)ethyl]-1,3,4,5-tetrahydro-2H-imidazol-2-one; or
1-[2-(3,4-dimethoxyphenyl)ethyl]-3-phenylmethyl-1,3,4,5-tetrahydro-2H-imidazol-2-one.

The subgroups as defined hereinafter are described as subgroups of the compounds of formula (I) and are meant to be also subgroups of the compounds of formula (I').

A first set of particular groups of compounds of formula (I) or of compounds of formula (I') consists of those wherein one or more of the following provisions apply:

a) $R^1$ is hydrogen; $C_{1-6}$alkyl; difluoromethyl; $C_{3-6}$cycloalkyl; tetrahydrofuranyl; bicyclo[2.2.1]-2-heptenyl; arylsulfonyl; or $C_{1-10}$alkyl substituted with $C_{3-7}$cycloalkyl or tetrahydrofuranyl; and $R^2$ is $C_{1-6}$alkyl, difluoromethyl or trifluoromethyl;

b) $R^3$ is hydrogen;

c) $R^4$ is hydrogen, $C_{1-6}$alkyl, $C_{3-6}$-cycloalkyl, hydroxy, $C_{1-6}$alkyloxy, trifluoromethyl, halo, amino, cyano$C_{1-6}$-alkyl, $C_{1-6}$alkylcarbonylamino, aryl, aryl$C_{1-6}$alkyl, $Het^1C_{1-6}$alkyl and $R^5$ is hydrogen, $C_{1-6}$alkyl or hydroxy, preferably $R^4$ and $R^5$ each independently are hydrogen or $C_{1-6}$alkyl;

d) $R^4$ and $R^5$ are taken together to form a radical of formula (b–1) or (b–2), preferably a radical of formula (b–1) wherein n is 2;

e) Y is a direct bond, methylene or 1,2-ethanediyl, preferably Y is methylene;

f) L is hydrogen, $C_{1-6}$alkyl, optionally substituted $C_{3-6}$alkenyl, $C_{1-6}$alkyloxycarbonyl, $C_{1-6}$alkyloxycarbonyl$C_{1-6}$alkyl or aryl$C_{1-6}$alkyl, preferably L is hydrogen;

g) —A—B— is a bivalent radical of formula (c–1) or (c–2), preferably a bivalent radical of formula (c–1) wherein $R^9$ and $R^{10}$ are both hydrogen.

An interesting subgroup within said first set of groups consists of those compounds of formula (I) or of compounds of formula (I') wherein $R^1$ is $C_{1-6}$alkyl, $C_{3-6}$cycloalkyl or $C_{1-10}$alkyl substituted with $C_{3-7}$cycloalkyl and $R^2$ is $C_{1-6}$alkyl.

Another interesting subgroup within said first set of groups consists of those compounds of formula (I) or of compounds of formula (I') wherein Y is methylene.

A second set of particular groups of compounds of formula (I) or of compounds of formula (I') consists of those wherein one or more of the following provisions apply:
1) $R^1$ is hydrogen; a saturated 5-, 6- or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen;
2) $R^2$ is hydrogen, $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- and 7-membered heterocycle containing one or two heteroatoms selected from oxygen, sulfur or nitrogen;
3) $R^3$ is halo or $C_{1-6}$alkyloxy;
4) $R^4$ halo; trifluoromethyl; $C_{3-6}$cycloalkyl; $C_{3-6}$cycloalkylaminocarbonyl; aryl; $Het^1$; or $C_{1-6}$alkyl substituted with cyano, amino, hydroxy, $C_{1-4}$alkylcarbonylamino, aryl or $Het^1$; or
$R^4$ is a radical of formula:

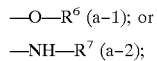

wherein
$R^6$ is $C_{1-6}$alkyl substituted with hydroxy, carboxyl, $C_{1-4}$alkyloxy-carbonyl, amino, mono- or di($C_{1-4}$alkyl)amino, $Het^1$ or aryl;
$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;
5) $R^5$ is halo;
6) $R^5$ is hydroxy and $R^4$ is other than hydrogen or $C_{1-6}$alkyl;
7) $R^4$ and $R^5$ taken together form a bivalent radical of formula:

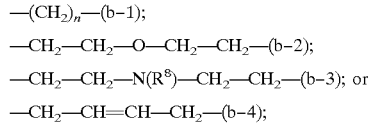

wherein
n is 2, 3, 4 or 5;
$R^8$ is hydrogen, $C_{1-6}$alkyl, $C_{1-6}$alkylsulfonyl or p-toluenesulfonyl;
8) —A—B— is a bivalent radical of formula (c–2);
9) L is $C_{1-6}$alkyl substituted with hydroxy or $C_{1-4}$alkyloxy; $C_{3-6}$alkenyl; $C_{3-6}$alkenyl substituted with aryl; $C_{1-6}$alkylsulfonyl or arylsulfonyl.

An interesting subgroup within said second set of groups consists of those compounds of formula (I) or of compounds of formula (I') wherein $R^4$ is halo; trifluoromethyl; $C_{3-6}$cycloalkyl; $C_{3-6}$cycloalkylaminocarbonyl; aryl; $Het^1$; or $C_{1-6}$alkyl substituted with cyano, amino, hydroxy, $C_{1-4}$alkylcarbonylamino, aryl or $Het^1$; or $R^4$ is radical of formula:

—O—$R^6$ (a-1); or

—NH—$R^7$ (a-2);

wherein
$R^6$ is $C_{1-6}$alkyl substituted with hydroxy, carboxyl, $C_{1-4}$alkyloxycarbonyl, amino, mono- or di($C_{1-4}$alkyl)amino, $Het^1$ or aryl;
$R^7$ hydrogen; $C_{1-6}$alkyl; $C_{1-4}$alkylcarabonyl; $C_{1-6}$alkyl substituted with hydroxy, carboxyl, $C_{1-4}$alkyloxycarbonyl, amino, mono- or di($C_{1-4}$alkyl)amino, $Het^1$ or aryl; or $R^5$ is halo; or $R^4$ and $R^5$ taken together form a bivalent radical of formula:

—$(CH_2)_n$—(b-1);

—$CH_2$—$CH_2$—O—$CH_2$—$CH_2$—(b-2);

—$CH_2$—$CH_2$—N($R^8$)—$CH_2$—$CH_2$—(b-3); or

—$CH_2$—CH=CH—$CH_2$—(b-4);

$R^8$ is hydrogen, $C_{1-6}$alkyl, $C_{1-6}$alkylsulfonyl or p-toluenesulfonyl.

Another interesting subgroup within said second set of groups consists of those compounds of formula (I) or of compounds of formula (I') wherein $R^1$ is hydrogen; a saturated 5-, 6- or 7-membered heterocycle containing one or two heteroatoms selected form oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen.

A third set of particular groups of compounds of formula (I) or of compounds of formula (I') consists of those wherein one or more of the following provisions apply:

1) $R^1$ is hydrogen; $C_{1-6}$alkyl; difluoromethyl; trifluoromethyl; a saturated 5-, 6- or 7- membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

2) $R^2$ is hydrogen; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

3) $R^4$ is halo; $C_{3-6}$cycloalkyl; $C_{3-6}$cycloalkylaminocarbonyl; aryl; $Het^1$; or $C_{1-6}$alkyl substituted with amino, $C_{1-4}$alkylcarbonylamino, aryl or $Het^1$; or substituted with amino, $C_{1-4}$alkylcarbonylamino, aryl or $Het^1$; or $R^4$ is a radical of formula:

—O—$R^6$ (a-1); or

—NH—$R^7$ (a-2);

wherein
$R^6$ is $C_{1-6}$alkyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;
$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

4) $R^5$ is halo;

5) $R^4$ and $R^5$ taken together form a bivalent radical of formula:

—$(CH_2)_n$—(b-1);

—$CH_2$—$CH_2$—O—$CH_2$—$CH_2$—(b-2);

—$CH_2$—$CH_2$—N($R^8$)—$CH_2$—$CH_2$—(b-3); or

—$CH_2$—CH=CH—$CH_2$—(b-4);

wherein
n is 2, 3, 4 or 5;
$R^8$ is hydrogen, $C_{1-6}$alkyl, $C_{1-6}$alkylsulfonyl or p-toluenesulfonyl;

6) —A—B— is a bivalent radical formula (c-2).

An interesting subgroup within said third set of groups consists of those compounds of formula (I) or of compounds of formula (I') wherein $R^4$ is halo; $C_{3-6}$cycloalkyl; $C_{3-6}$cycloalkylaminocarbonyl; aryl; $Het^1$; or $C_{1-6}$alkyl substituted with amino, $C_{1-4}$alkylcarbonylamino, aryl or $Het^1$; or $R^4$ is a radical of formula:

—O—$R^6$ (a-1); or

—NH—$R^7$ (a-2);

wherein
$R^6$ is $C_{1-6}$alkyl; $C_{1-6}$alkyl substituted with hydroxy, carboxyl, $C_{1-4}$alkyl-oxycarbonyl, amino, mono- or di($C_{1-4}$alkyl)amino, $Het^1$ or aryl;
$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, Het1 or aryl; or $R^5$ is halo; or $R^4$ and $R^5$ taken together form a bivalent radical of formula:

—$(CH_2)_n$—(b-1);

—$CH_2$—$CH_2$—O—$CH_2$—$CH_2$—(b-2);

—$CH_2$—$CH_2$—N($R^8$)—$CH_2$—$CH_2$—(b-3); or

—$CH_2$—CH=CH—$CH_2$—(b-4);

wherein
n is 2, 3, 4 or 5;
$R^8$ is hydrogen, $C_{1-6}$alkyl, $C_{1-6}$alkylsulfonyl or ρ-toluenesulfonyl;

Another interesting subgroup within said third set of groups consists of those compounds of formula (I) or of compounds of formula (I') wherein $R^1$ is hydrogen; $C_{1-6}$alkyl; difluoromethyl; trifluoromethyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

A fourth set of particular groups of compounds of formula (I) or of compounds of formula (I') consists of those wherein one or more of the following provisions apply:

1) $R^1$ is hydrogen; a saturated 5- 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

2) $R^2$ is hydrogen; $C_{3-6}$cyloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5- 6- or 7-membered heterocycle containing one or two heteroatoms selected from oxygen, sulfur or nitrogen;

3) $R^4$ is $C_{1-6}$alkyl; trifluoromethyl; $C_{3-6}$cycloalkyl; carboxyl; $C_{1-4}$alkyloxycarbonyl; $C_{3-6}$cycloalkylaminocarbonyl; or $C_{1-6}$alkyl substituted with cyano, amino, hydroxy, $C_{1-4}$alkylcarbonylamino; or $R^4$ is a radical of formula:

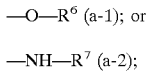

—O—$R^6$ (a-1); or

—NH—$R^7$ (a-2);

wherein
$R^6$ is $C_{1-6}$alkyl substituted with carboxyl, $C_{1-4}$alkyloxycarbonyl, amino, mono- or di($C_{1-4}$alkyl)amino, Het$^1$ or aryl;
$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, Het$^1$ or aryl;

4) $R^5$ is $C_{1-6}$alkyl;

5) $R^4$ and $R^5$ taken together form a bivalent radical of formula:

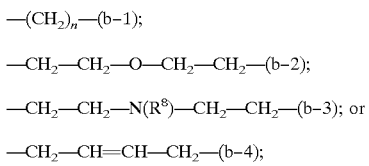

—(CH$_2$)$_n$—(b-1);

—CH$_2$—CH$_2$—O—CH$_2$—CH$_2$—(b-2);

—CH$_2$—CH$_2$—N($R^8$)—CH$_2$—CH$_2$—(b-3); or

—CH$_2$—CH=CH—CH$_2$—(b-4);

wherein
n is 2, 3, 4 or 5;
$R^8$ is hydrogen, $C_{1-6}$alkyl, $C_{1-6}$alkylsulfonyl or p-toluenesulfonyl;

6) —A—B— is a bivalent radical of formula (c-2).

An interesting subgroup within said fourth set of groups consists of those compounds of formula (I) or of compounds or formula (I') wherein $R^4$ is $C_{1-6}$alkyl; trifluoromethyl; $C_{3-6}$cyloalkyl; carboxyl; $C_{1-4}$alkyloxycarbonyl; $C_{3-6}$cycloalkylaminocarbonyl; or $C_{1-6}$alkyl substituted with cyano, amino, hydroxy, $C_{1-4}$alkylcarbonylamino; or $R^4$ is a radical of formula:

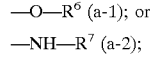

—O—$R^6$ (a-1); or

—NH—$R^7$ (a-2);

wherein
$R^6$ is $C_{1-6}$alkyl substituted with carboxyl, $C_{1-4}$alkyloxycarbonyl, amino, mono- or di($C_{1-4}$alkyl)amino, Het$^1$ or aryl;
$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, Het$^1$ or aryl; or $R^5$ is $C_{1-6}$alkyl; or $R^4$ and $R^5$ taken together form a bivalent radical of formula:

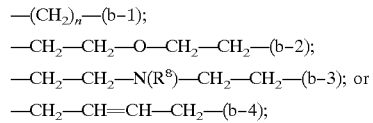

—(CH$_2$)$_n$—(b-1);

—CH$_2$—CH$_2$—O—CH$_2$—CH$_2$—(b-2);

—CH$_2$—CH$_2$—N($R^8$)—CH$_2$—CH$_2$—(b-3); or

—CH$_2$—CH=CH—CH$_2$—(b-4);

wherein
n is 2, 3, 4 or 5;
$R^8$ is hydrogen, $C_{1-6}$alkyl, $C_{1-6}$alkylsulfonyl or p-toluenesulfonyl.

Another interesting subgroup within said fourth set of groups consists of those compounds of formula (I) or of compounds of formula (I') wherein $R^1$ hydrogen; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]-heptenyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5- 6- or 7-membered heterocycle containing one or two heteroatoms selected from oxygen, sulfur or nitrogen.

Preferred compounds are those compounds of formula (I) or of compounds of formula (I') wherein $R^4$ is $C_{3-6}$cycloalkyl; $C_{3-6}$cycloalkylaminocarbonyl; or $C_{1-6}$alkyl substituted with amino or $C_{1-4}$alkylcarbonylamino; or $R^4$ is a radical of formula:

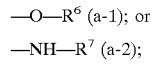

—O—$R^6$ (a-1); or

—NH—$R^7$ (a-2);

wherein
$R^6$ is $C_{1-6}$alkyl substituted with carboxyl, $C_{1-4}$alkyloxycarbonyl, amino, mono- or di($C_{1-4}$alkyl)amino, Het$^1$ or aryl;
$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{C1-4}$alkyl)amino, Het$^1$ or aryl; or $R^4$ and $R^5$ taken together form a bivalent radical of formula:

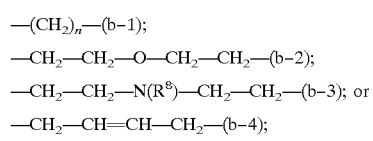

—(CH$_2$)$_n$—(b-1);

—CH$_2$—CH$_2$—O—CH$_2$—CH$_2$—(b-2);

—CH$_2$—CH$_2$—N($R^8$)—CH$_2$—CH$_2$—(b-3); or

—CH$_2$—CH=CH—CH$_2$—(b-4);

wherein
n is 2, 3, 4 or 5;
$R^8$ is hydrogen, $C_{1-6}$alkyl, $C_{1-6}$alkylsulfonyl or p-toluenesulfonyl.

Also preferred compounds are those compounds of formula (I) or of compounds of formula (I') wherein $R^1$ is hydrogen; a saturate 5-, 6- or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cyloalkyl and a saturated 5-, 6- or 7-membered heterocycle containing one or two heteroatoms selected from oxygen, sulfur or nitrogen.

More preferred compounds are those compounds of formula (I) or of compounds of formula (I') wherein $R^1$ is $C_{3-6}$cycloalkyl or methyl substituted with $C_{3-7}$cycloalkyl, $R^2$ is $C_{1-6}$alkyl, $R^3$ is hydrogen, $R^4$ is $C_{1-6}$alkyl, $R^5$ is hydrogen or $C_{1-6}$alkyl, or $R^4$ and $R^5$ are taken together to form a radical of formula (b-1) wherein n is 2, Y, —A—B— is a bivalent radical of formula (c-1) wherein $R^9$ and $R^{10}$ are both hydrogen, Y is methylene and L is hydrogen.

Most preferred compounds are selected from:
1-[[1-[3-(cyclopentyloxy)-4-methoxyphenyl] cyclopropyl]methyl]-1,3-dihydro-2H-imidazol-2-one; 1-[2-[3-(cyclopentyloxy)-4-methoxyphenyl]-2-methylpropyl]-1,3-di hydro-2H-imidazol-2-one; 1-[2-[3-(cyclopentyloxy)-4-methoxyphenyl]propyl]-1,3-dihydro-2H-imidazol-2-one; and 1-[2-[3-(cyclopropylmethoxy)-4-methoxyphenyl]-propyl]-1,3-dihydro-2H-imidazol-2-one; the pharmaceutically acceptable acid or base addition salts and the stereochemically isomeric forms thereof.

Whenever used hereinafter, $R^1$ to $R^{10}$, —A—B— and L are defined as under formula (I) unless otherwise indicated.

The compounds of formula (I) can generally be prepared by N-alkylating a 1,3-dihydro-2H-imidazol-2-one derivative of formula (II) with an appropriately substituted alkylating agent of formula (III), wherein $W^1$ is a reactive leaving group such as, for example, a halogen.

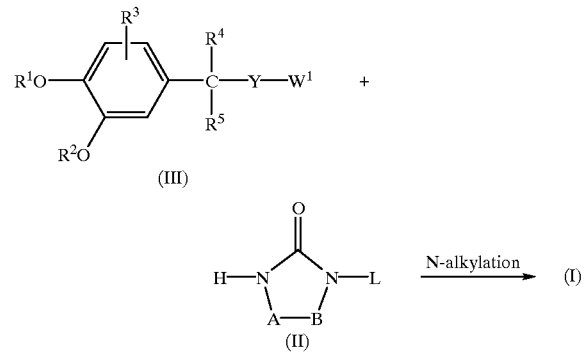

Said N-alkylation may conveniently be performed in the presence of a base such as, for example, sodium hydride, butyllithium or sodium bis(trimethylsilyl)amide, in a reaction-inert solvent such as, for example, tetrahydrofuran, optionally cooled on the ice-bath. The reaction is preferably performed under a reaction inert atmosphere such as, for example, oxygen free nitrogen. It may be advantageous to add to the reaction mixture a crown ether, e.g., 1,4,7,10,13, 16-hexaoxacyclooctadecane and the like or a complexing agent such as for example, tris[2-(2-methoxyethoxy)] ethanamine and the like. Stirring may enhance the rate of the reaction. In case intermediates of formula (II), wherein L is replaced by a suitable protecting group, are used in said N-alkylation reaction, compounds of formula (I) wherein L is hydrogen, said compounds being represented by compounds of formula (I-a), may be obtained using art-known deprotection reactions.

In this and following preparations, the reaction products may be isolated from the reaction medium and, if necessary, further purified according to methodologies generally known in the art such as, for example, extraction, crystallization, trituration and chromatography.

Alternatively, compounds of formula (I) may be prepared by reacting an organometallic intermediate of formula (IV), wherein M is an appropriate metal ion or metalcomplex ion such as, for example, $Li^+$, $(MgBr)^+$, $B(OH)_2^+$or $Sn(CH_3)_3^+$, with a suitable 1,3-dihydro-2H-imidazol-2-one derivative of formula (V) wherein $W^2$ is a reactive leaving group such as, for example, a halogen. In case $R^4$ and $R^5$ are taken together and form a radical of formula (b-1), (b-2), (b-3) or (b-4), $W^2$ may also be a cyanide moiety provided that the intermediate of formula (IV) is a Grignard reagent.

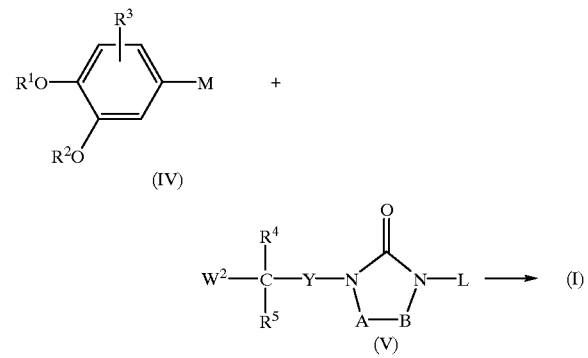

Said reaction may be performed in a reaction-inert solvent such as, for example, dimethoxyethane, tetrahydrofuran or diethylether. Stirring and heating may enhance the rate of the reaction. In case intermediates of formula (V), wherein L is replaced by a suitable protecting group, are used in said reaction, compounds of formula (I) wherein L is hydrogen, said compounds being represented by compounds of formula (I-a), may be obtained using art-known deprotection reactions.

Compounds of formula (I-a) wherein —A—B— is a radical of formula (c-1), said compounds being represented by formula (I-a-1), can conveniently be prepared by cyclization of an intermediate of formula (VI) or a functional derivative thereof in the presence of a suitable acid such as, for example, hydrochloric acid.

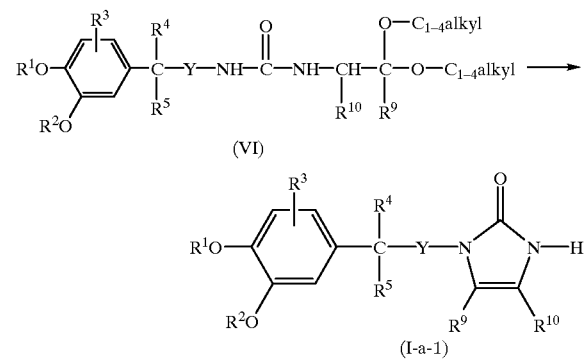

Said cyclization may be performed in a reaction inert solvent such as, for example, water, methanol or a mixture thereof. Stirring and heating may enhance the rate of the reaction.

In particular, compounds of formula (I-a-1) wherein $R^5$ is hydroxy and Y is methylene, said compounds being represented by formula (I-a-1-1), may be prepared by cyclization of an intermediate of formula (VI-I) wherein P is hydrogen or, preferably, is a trimethylsilyl protecting group or a functional derivative thereof, in a manner analogous to the one described for the preparation of a compound of formula (I-a-1) from an intermediate of formula (VI).

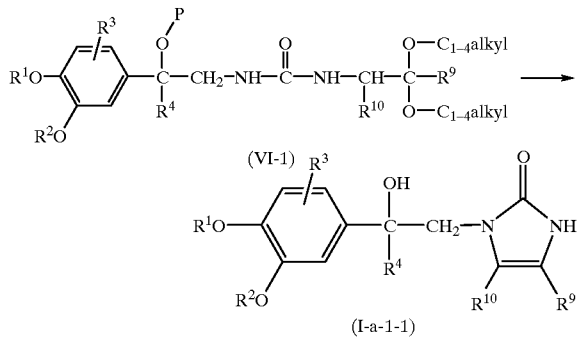

Compounds of formula (I-a-1) may also be prepared by cyclization of an intermediate of formula (VII) or a functional derivative thereof in the presence of a suitable isocyanate, such as, for example, potassium isocyanate or trimethylsilyl isocyanate.

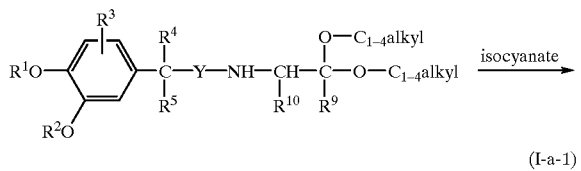

Alternatively, compounds of formula (I-a-1) may also be prepared by reacting an intermediate of formula (VII) with a suitable cyanide such as, for example, potassium cyanide, thus obtaining the corresponding N-Cyanide derivative which may be further hydrolyzed in the presence of an acid such as, for example, hydrochloric acid, keeping the pH of the reaction mixture basic. The thus formed corresponding ureum derivative is then further cyclized in the presence of an excess of an acid such as, for example, hydrochloric acid, to a compound of formula (I-a-1).

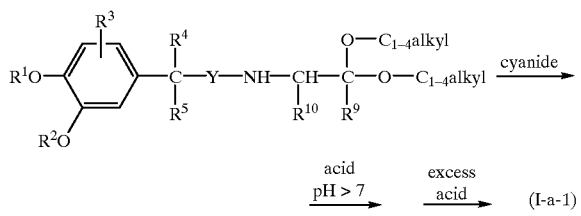

Compounds of formula (I-a) wherein —A—B— is a radical of formula (c-2), said compounds being represented by formula (I-a-2), can be obtained by cyclization of an intermediate of formula (VIII) or a functional derivative thereof in the presence of a suitable reagent such as, for example, phosgene, ureum or N,N'-carbonyldiimidazole.

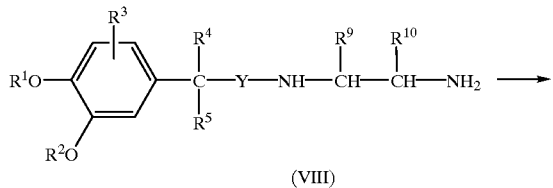

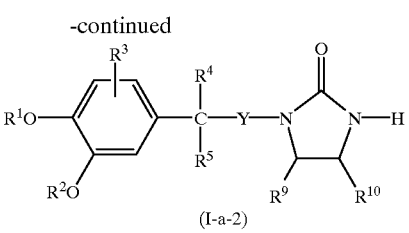

The compounds of formula (I) can also be converted into each other following art-known procedures of functional group transformation.

For example, compounds of formula (I) wherein L is other than hydrogen, said compounds being represented by formula (I-b), may be prepared by reacting a compound of formula (I-a) with L"-$W^3$ (IX), wherein L" is the same as L defined under formula (I) but other than hydrogen and $W^3$ is a reactive leaving group such as, for example, a halogen atom.

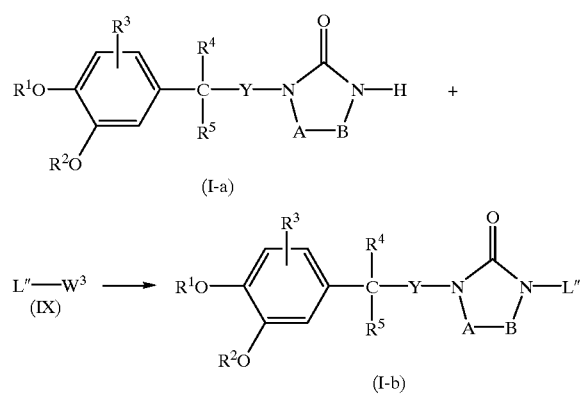

Also, art-known addition reactions may be used to convert compounds of formula (I-a) into compounds of formula (I-b).

Compounds of formula (I-b) wherein —A—B— is a radical of formula (c-2), said compounds being represented by formula (I-b-2), can be prepared by hydrogenation of compounds of formula (I-b) wherein —A—B— is a radical of formula (c-1), said compounds being represented by formula (I-b-1), using art-known hydrogenation techniques. For instance, hydrogen in the presence of a suitable catalyst such as, for example, palladium or platinum supported on for instance charcoal may be used as an appropriate hydrogenation agent.

Compounds of formula (I-a-1) can be prepared by dehydrogenation of compounds of formula (I-a-2) using art-known dehydrogenation techniques. For instance, refluxing a compound of formula (I-a-2) in a reaction-inert solvent such as, for example, ρ-xylene, in the presence of a suitable catalyst such as, for example, palladium or platinum supported on for instance charcoal may be used as a dehydrogenation technique.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Intermediates mentioned hereinabove may be prepared following art-known techniques.

In particular, intermediates of formula (VI) may be prepared by first N-acylating an amine of formula (X) with phenyl chloroformate or a functional derivative thereof. Said N-acylation can conveniently be performed in a reaction inert solvent such as, for example, dichloromethane, benzene or toluene, optionally cooled on an ice-bath, and in the presence of a base such as, for example, N,N-diethylethanamine or sodium-bicarbonate. The thus obtained intermediate may be subsequently reacted with 2,2-(di-$C_{1-4}$alkyloxy)ethanamine or a functional derivative thereof, to form an intermediate of formula (VI). Said reaction can conveniently be performed in a reaction inert solvent such as, for example, 1,4-dioxane, in the presence of a catalyst such as, for example, N,N-diethyl ethanamine, and optionally in the presence of a catalyst such as, for example, N,N-dimethyl-pyridinamine. Stirring and elevated temperatures may enhance the rate of the reaction.

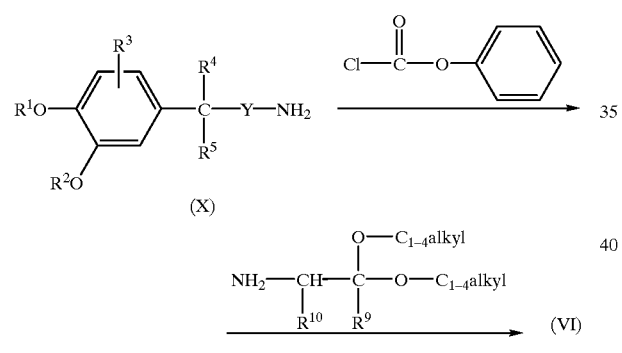

Also, intermediates of formula (VI) may be directly formed by reacting an intermediate of formula (X) with a suitable reagent such as, for example, 2,2-(di$C_{1-4}$alkyloxy)-ethanisocyanate, phenyl [2,2-di($C_{1-6}$alkyloxy)]ethyl) carbamate or a functional derivative of any one of said reagents.

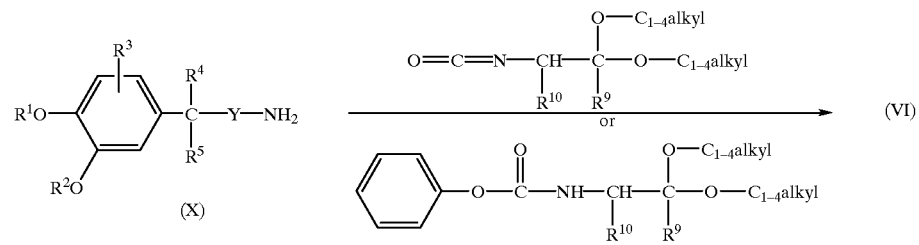

In particular, intermediates of formula (VI-1) may be prepared by reacting an intermediate of formula (X) wherein $R^5$ is a hydroxy group or, preferably, a protected hydroxy group, the protective group P being a trimethylsilyl protecting group or a functional derivative thereof, and Y is methylene, said intermediates being represented by formula (X-1), with N-[2,2-di($C_{1-4}$alkyl)ethyl]-1H-imidazole-1-carboxamide or a functional derivative thereof.

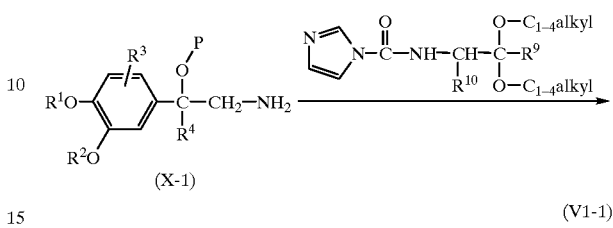

Intermediates of formula (VII) can be prepared by reacting an amine of formula (X) with an intermediate of formula (XI) wherein $W^4$ is a reactive leaving group such as, for example, a halogen.

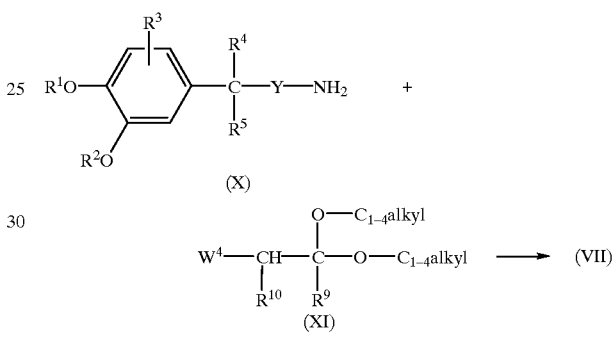

Alternatively, intermediates of formula (VII) may be prepared by reacting an intermediate of formula (III) with 2,2-(di$C_{1-4}$alkyloxy)ethanamine or a functional derivative thereof.

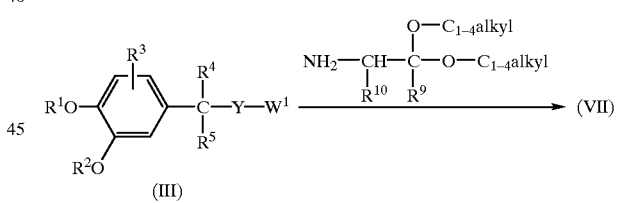

Some of the intermediates of formula (X) are described in WO 92/00968, WO 93/15044 and WO 93/15045.

In particular, intermediates of formula (X) may be prepared by reacting an intermediate of formula (III) with an intermediate of formula (XII) wherein M is an appropriate metal ion or metalcomplex ion such as, for example, Li$^+$ or (MgBr)$^+$, and P is a suitable protecting group such as, for example, (1,1-dimethylethyl)oxycarbonyl. The thus obtained protected intermediates of formula (X) may subsequently be deprotected by art-known techniques such as, for example, acid hydrolysis.

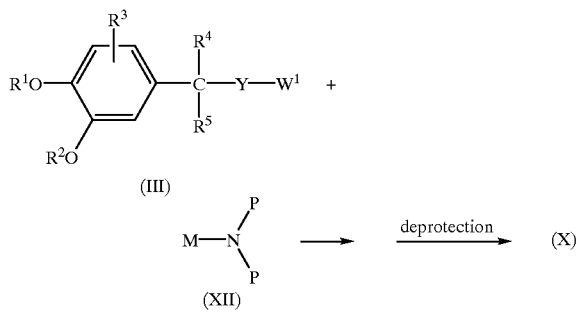

Intermediates of formula (X) wherein Y is a direct bond or $C_{1-3}$ alkanediyl, said Y being represented by Y', and said intermediates being represented by formula (X'), may be prepared by reducing the unsaturated carbon-nitrogen bond in the intermediates of formula (XIII) with a suitable reducing agent such as, for example, lithium aluminum hydride or hydrogen in the presence of a catalyst such as, for example, Raney nickel. The cyanide moiety in the intermediates of formula (XIII) may also be replaced by a functional derivative thereof such as, for example, an oxime moiety.

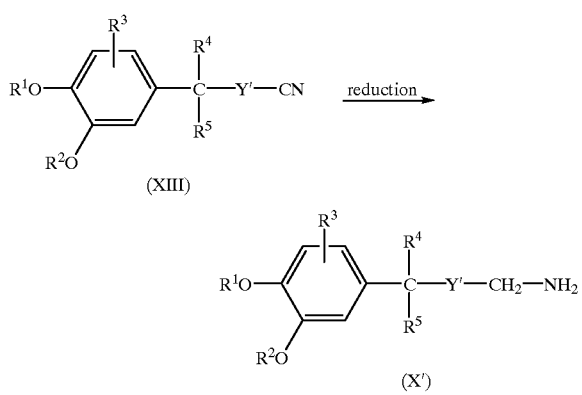

Some of the intermediates of formula (XIII) are described in WO 92/00968, WO 93/15044 and WO 93/15045.

In particular, intermediates of formula (XIII) wherein $R^4$ and $R^5$ are taken together to form a radical of formula (b-1) and Y' is a direct bond, said intermediates being represented by formula (XIII-b), may be prepared by reacting an intermediate of formula (XIII) wherein —C($R^4R^5$)—Y'— is —CH$_2$—, said intermediates being represented by formula (XIII-a), with W$^6$—(CH$_2$)$_n$—W$^6$ (XV) wherein W$^6$ is a reactive leaving group such as, for example, a halogen, and n is 2, 3, 4 or 5.

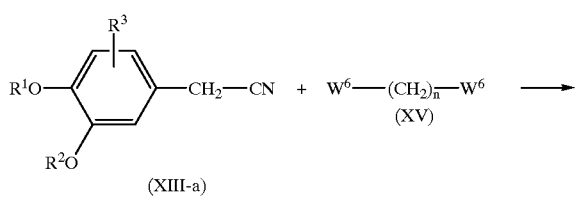

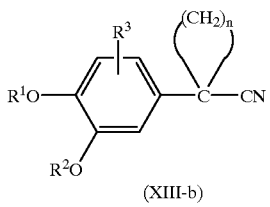

Said reaction may conveniently be performed in a reaction inert solvent such as, for example, water, tetrahydrofuran or dimethylsulfoxide, and in the presence of benzyltriethytammonium chloride and a base such as, for example, sodium hydroxide. Stirring and elevated temperatures may enhance the rate of the reaction.

Intermediates of formula (X) wherein Y is methylene and $R^5$ is hydrogen, said intermediates being represented by formula (X-a), may be prepared by reducing a nitro derivative of formula (XIV) with a suitable reducing agent such as, for example, lithium aluminium hydride.

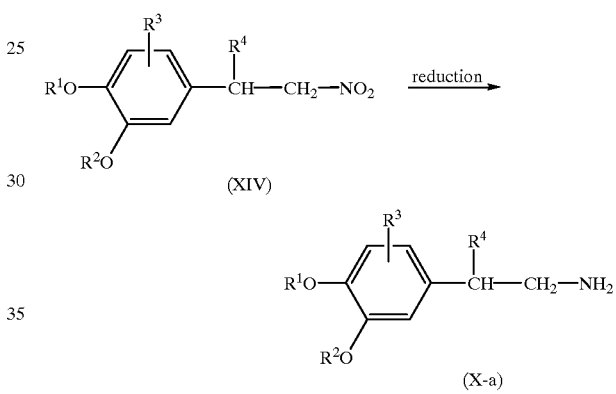

Intermediates of formula (X-1) may be prepared by reacting an intermediate of formula (XVI), wherein $R^4$ is restricted to those moieties that do not interfere with the reaction such as, for example, hydrogen, optionally substituted $C_{1-6}$ alkyl, $C_{3-6}$ cycloalkyl, aryl and Het$^1$, with trimethylsilyl cyanide or a functional derivative thereof in the presence of a suitable catalyst such as, for example, zinc iodide, and in a reaction-inert solvent such as, for example, dichloromethane; thus forming an intermediate of formula (XIII) wherein Y' is a direct bond and $R^5$ is hydroxy or, preferably, a protected hydroxy group, the protective group P being a trimethylsilyl protecting group or a functional derivative thereof, said intermediates being represented by formula (XIII-c). Subsequently, the nitrile derivative of formula (XIII-c) may be reduced to the corresponding amine of formula (X-1) using art-known techniques such as, for example, reduction with hydrogen in the presence of a suitable catalyst such as, for example, Raney nickel.

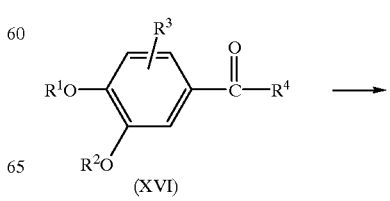

-continued

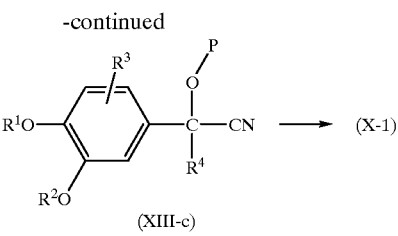

(XIII-c)

The compounds of formula (I), the N-oxide forms, the pharmaceutically acceptable acid or base addition salts and the stereochemically isomeric forms thereof, are potent inhibitors of the phosphodiesterase (PDE) isoenzymes of family IV (cAMP-specific family).

cAMP (adenosine cyclic 3',5'-monophosphate) is a key second messenger, the concentration of which affects particular cell activities through activation of enzymes such as kinases. PDE IV is known to hydrolyse cAMP to its corresponding inactive 5'-monophosphate metabolite. Hence, inhibition of PDE IV leads to an elevation of cAMP levels in particular cells such as the respiratory smooth muscle cell and in a wide variety of inflammatory cells, i.e. certain lymphocytes, e.g. basophils, neutrophils and eosinophils, monocytes and mast-cells. A number of allergic, atopic and inflammatory diseases are deemed to be caused by higher-than-normal PDE IV concentrations which result in low cAMP levels and hypersensitivity of the thus affected cells for excitatory stimuli. (Examples of said hypersensitivity are for example, excessive histamine release from basophils and mast cells or excessive superoxide anion radical formation by eosinophils.) Hence, the present compounds having potent phosphodiesterase IV inhibitory properties are deemed useful agents in alleviating and/or curing allergic, atopic and inflammatory diseases. The functional effects of PDE IV inhibitors are e.g. respiratory smooth muscle relaxation, bronchodilation, platelet aggregation inhibition and inhibition of white blood cell mediator release. Examples of allergic diseases are bronchial asthma, cheilitis conjunctivitis, contact dermatitis and eczema, irritable bowel disease, deshydroform eczema, urticaria, vasculitis, vulvitis; examples of atopic diseases are dermatitis and eczema, winterfeet, asthma, allergic rhinitis; and related afflictions are, for example, psoriasis and other hyperproliferative diseases.

The present invention thus also relates to compounds of formula (I) as defined hereinabove for use as a medicine, in particular for use as an anti-asthmatic medicine or as a medicine for treating atopic diseases. Thus the compounds of the present invention may be used for the manufacture of a medicament for treating asthmatic or atopic diseases more; in particular atopic dermatitis.

The PDE IV inhibitory activity of the compounds of formula (I) may be demonstrated in the test "Inhibition of recombinant human mononuclear lymphocyte (MNL) phosphodiesterase type IV B produced in insect cells with a baculovirus vector". Several in vivo and in vitro tests may be used to demonstrate the usefulness of the compounds of formula (I) in treating the described allergic, atopic and inflammatory diseases. Such tests are for instance, "Bronchoconstriction of the guinea pig trachea in vitro", "Bronchoconstriction of the guinea pig trachea in vivo" and the in vivo test "Dextraninduced oedema formation in mouse ear".

Further, the present compounds have only very low inhibitory activity on the phosphodiesterase isoenzymes of family III (cGMP-inhibited family). Inhibition of, in particular, PDE III leads to an elevation of cAMP in Ie cardiac muscle, thereby causing effects on the contractile force of the heart as well as on the relaxation of the heart. In the treatment of the described allergic, atopic and inflammatory diseases, cardiovascular effects clearly are undesired. Hence, as the present compounds inhibit PDE IV at much lower concentrations as they inhibit PDE III, their therapeutic use may be adjusted to avoid cardiovascular side-effects.

Art-known PDE IV inhibitors often cause adverse gastro-intestinal side effects. Most of the present compounds, however, have few effects on the gastro-intestinal tract, which may be demonstrated in the test "Gastric emptying of a caloric meal in rats".

The designation PDE III and IV as used herein refers to the classification by J. A. Beavo and D. H. Reifsnyder, TIPS Reviews, April 1990, pp. 150–155.

The compounds of the present invention also have cytokine inhibitory activity. A cytokine is any secreted polypeptide that affects the function of other cells by modulating interactions between cells in the immune or inflammatory response. Examples of cytokines are monokines and lymphokines and they may be produced by a wide variety of cells. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and β-lymphocytes. Lymphokines am generally referred to as being produced by lymphocyte cells. Examples of cytokines include Interleukin-1 (IL-1), Interleukin-2 (IL-2), Interleukin-6 (IL-6), Interleukin-8 (IL-8), alpha-Tumor Necrosis Factor (αTNF) and beta-Tumor Necrosis Factor (βTNF).

The cytokine specifically desired to be inhibited is αTNF Excessive or unregulated TNF production is implicated in mediating or exacerbating a number of diseases including rheumatoid arthritis, rheumatoid spondylitis, osteoartritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, or pyresis.

The cytokine inhibitory activity of the compounds of formula (I), such as the inhibition of αTNF production, may be demonstrated in the in vitro test "Cytokine production in human whole blood cultures".

In addition, the compounds of the present invention are expected to show no or little endocrinological side-effects. This may be evidenced by, for instance, the "Testosterone in vivo" test the "In vitro inhibition of the aromatase activity"-test and the "In vivo inhibition of the aromatase activity"-test. In view of their useful PDE IV and cytokine inhibiting properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, topically, percutaneously, by inhalation or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

It is especially advantageous to formulate the aforementioned pharmaceutical compositions in dosage unit form for ease of administration and uniformity of dosage. Dosage unit form refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

In general it is contemplated that an effective daily amount would be from 0.01 mg/kg to 10 mg/kg body weight, more preferably from 0.04 mg/kg to 5 mg/kg body weight. It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention.

Experimental part

Compounds of formula (I) and some intermediates have a stereogenic center. In those cases where the racemate was separated into its enantiomers, the stereochemically isomeric form which was first isolated was designated as "A" and the second as "B", without further reference to the actual stereochemical configuration. Hereinafter, "DIPE" means diisopropylether, "DMF" means N,N-dimethylformamide and "THF" means tetrahydrofuran.

A. Preparation of the intermediates

EXAMPLE A.1 a) Under a $N_2$ flow, a solution of benzyltrimethylammonium dichloroiodate (78 g) in THF (250 ml) was added to a mixture of 1-[3-(cyclopentyloxy)-4-methoxyphenyl]ethanone (26.3 g) in THF (250 ml) while stirring. The resulting reaction mixture was stirred for 16 hours at RT. The solvent was evaporated and the residue was redissolved in diethyl ether (300 ml). The mixture was added dropwise to a 5% $Na_2S_2O_4$ solution (400 ml). The aqueous layer was extracted twice with diethyl ether (100 ml). The combined organic layers were washed twice with water (500 ml), dried ($MgSO_4$), filtered and the solvent evaporated. The crude oil was crystallized from hexane. The precipitate was filtered off, washed with hexane and dried, yielding 11 g of 2-chloro-1-[3-(cyclopentyloxy)-4-methoxyphenyl]ethanone. The filtrate was evaporated and the residue was crystallized from hexane. The precipitate was filtered off and dried, yielding 7.4 g (24.6%) of 2-chloro-1-[3-(cyclopentyloxy)-4-methoxyphenyl]ethanone (interm. 1).

b) Sodium bis(trimethylsilyl)amide (5 ml) was added to a solution of 1,3-dihydro-2H-imidazol-2-one (0.84 g) in DMF (50 ml), stirred under a $N_2$ flow and cooled in an ice-bath. The reaction mixture was stirred for 30 minutes. Intermediate 1 (2.69 g) was added portionwise and be resulting reaction mixture was stirred for 16 hours at RT, then for 2 hours at 50° C. The reaction mixture was stirred in methyl isobutyl ketone/water (200 ml/50 ml). The solvent was evaporated and methyl isobutyl ketone (100 ml) was added and azeotroped on the rotary evaporator. The mixture was purified by column chromatography over silica gel (eluent: $CH_2Cl_2/(CH_3OH/NH_3)$ 97/3). The desired fractions were collected and the solvent was evaporated. The white solid was stirred in diisopropyl ether, filtered off, washed with DIPE and dried, yielding 0.4 g (12.6%) of 1-[2-[3-(cyclopentyloxy)-4-methoxyphenyl]-2-oxo-ethyl]-1,3-dihydro-2H-imidazol-2-one (interm. 2; mp. 201.1° C).

In a similar way were prepared:

1-[2-(3,4-dimethoxyphenyl)-2-oxoethyl]-1,3-dihydro-3-(phenylmethyl)-2H-imidazol-2-one (interm. 21; mp. 128.8° C.); ethyl 3-[2-(3,4-dimethoxyphenyl)-2-oxoethyl]-2-oxo-1-imidazolidine-1-carboxylate (interm. 22).

EXAMPLE A.2 a) A mixture, of benzyltriethylammonium chloride (1.7 g) and sodium hydroxide (120 g) in water (50 ml) was stirred at 60–70° C. 3-Cyclopentyloxy-4-methoxybenzeneacetonitrile (56 g) and 1,2-dibromoethane (50 ml) were added dropwise and the mixture was stirred overnight. 1,2-Dibromoethane (2×25 ml) was added and the mixture was stirred overnight. THF (50 ml) and 1-2-dibromoethane (25 ml) were added and the mixture was stirred again overnight. 1,2-Dibromoethane (25 ml) was added and the mixture was stirred for 3 days. The mixture Ass diluted with water and DIPE. The separated organic layer was dried (MgSO4), filtered and the solvent evaporated, yielding 50.5 g of product. A sample (24.5 g) was stirred in petroleum ether and the precipitate was filtered off, washed and dried, yielding 17 g (31%) of 1-[3-(cyclopentyloxy)-4-methoxyphenyl]cyclopropanecarbonitrile (interm. 3; mp. 80.4° C.).

b) Under a $N_2$ flow, a mixture of intermediate 3 (3.7 g) in THF (50 ml) was added dropwise to a suspension of lithium aluminium hydride (0.55 g) in THF (50 ml), while stirring at 0° C. The resulting reaction mixture was stirred for one hour at RT, then for 2 hours at reflux temperature. The reaction mixture was cooled to 0° C. on an ice-bath. First water (0.6 ml) and then a 15% aqueous NaOH solution (0.6 ml) were added, then water (1.8 ml) was added again. The reaction mixture was filtered over dicalite and the filtrate was evaporated, yielding 3.76 g (100%) 1-[3-(cyclopentyloxy)-4-methioxyphenyl]cyclopropanemethanamine (interm. 4).

EXAMPLE A.3

A solution of 1-[3-(cyclopentyloxy)-4-methoxyphenyl]ethanone oxime (15.3 g) in methanol/ammonia (350 ml) was hydrogenated for 3 hours with Raney nickel (3 g) as a catalyst. After uptake of $H_2$, the catalyst was filtered off, washed with methanol and the filtrate was evaporated. Toluene was added and azeotroped on the rotary evaporator, yielding 14.45 g (100%) of (±)-3-(cyclopentyloxy)-4-methoxy-α-methylbenzenemethanamine (interm. 5).

EXAMPLE A.4 a) Sodium hydride (2.8 g) was washed with n-hexane under a $N_2$ flow. THF (300 ml) was added and the mixture was cooled to –5° C. à 0° C. (2-propanone/$CO_2$ bath). Diethyl (cyanomethyl)phosphonate (11.5 ml) was added dropwise while stirring The mixture was stirred for 5 minutes. A solution of 1-(3-cyclopentyloxy-4-methoxyphenyl)-ethanone (13.93 g) in TIT (30 ml) was added dropwise. Upon complete addition, the reaction mixture was allowed to warm to RT. The reaction mixture was poured out into ice-water/$NH_4Cl$ and this mixture was extracted with DIPE. The separated organic layer was dried (MgSO$_4$), filtered and the solvent was evaporated. The resultant oil was purified by column chromatography over silica gel (eluent: $CH_2Cl_2$/n-hexane 70/30, upgrading to, 90/10). The desired fractions were collected and the solvent was evaporated. Toluene was added and azeotroped on the rotary evaporator and the residue was crystallized, yielding 15.7 g (100%) of (A)-3-[3-cyclopentyloxy)-4-methoxyphenyl]-2-butenenitrile (interm. 6).

b) A mixture of intermediate 6 (12.5 g) in methanol/ammonia (350 ml) was hydrogenated at a temperature below 20° C. with Raney nickel (3 g) as a catalyst, After uptake of $H_2$, the catalyst was filtered off and the filtrate was evaporated. Toluene was added and azeotroped on the rotary evaporator, yielding 11.6 g (100%) of (±)-3-(cyclopentyloxy)-4-methoxy-λ-methylbenzenepropanamine, interm. 7).

EXAMPLE A.5 a) A mixture of 3-(cyclopentyloxy)-4-methoxybenzeneacetonitrile (20 g) in THF (200 ml) was stirred at –78° C. under a $N_2$ flow. N-(1-methylethyl)-2-propanamine lithium salt (45 ml) was added dropwise and the resulting mixture was stirred for 30 minutes at –78° C. Iodomethane (13.5 g) was added dropwise and the resulting reaction mixture was allowed to warm to RT. The reaction mixture was stirred for 2 hours. The mixture was quenched with a saturated aqueous $NH_4Cl$ solution (200 ml) and was extracted with $CH_2Cl_2$(3×100 ml). The separated organic layer was dried (MgSO$_4$), filtered and the solvent was evaporated, yielding 17.7 g (100%) of (±)-3-(cyclopentyloxy)-4-methoxy-α-methylbenzeneacetonitrile (interm. 8).

b) A mixture of intermediate 8 (17.7 g) in methanol/ammonia (100 ml) was hydrogenated at 20° C. with Raney nickel (3 g) as a catalyst. After uptake of $H_2$, the catalyst was filtered off and the filtrate was evaporated. Toluene was added and azeotroped on the rotary evaporator. The residue was purified by HPLC over Hypersil BDS (eluent: (0.5% ammonium acetate in $H_2O$)/$CH_3OH$/$CH_3CN$ 70/15/15, upgrading over 10/80/10, to 0/0/100). The pure fractions were collected and the solvent was evaporated, yielding 9.7 g (54%) of (±)-3-(cyclopentyloxy)-4-methoxy-β-methylbenzeneethanamine (interm. 9).

EXAMPLE A.6 a) A mixture of intermediate 9 (9.7 g) and triethylamine (4.34 g) in $CH_3Cl_2$(100 ml) was cooled on an ice-bath. Phenyl chloroformate (6.7 g) was added dropwise and the resulting reaction mixture was stirred for 48 hours at RT. Water (200 ml) was added and the mixture was stirred for 10 minutes. The organic layer was separated, dried (MgSO$_4$), filtered and the solvent was evaporated. The residue was purified by column chromatography over silica gel (eluent: $CH_2Cl_2$). The pure fractions were collected and the solvent was evaporated, yielding 11.2 g (78%) of (±)-phenyl [(2-[3-(cyclopentyloxy)-4-methoxyphenyl]propyl]carbamate (interm. 10).

b) A mixture of 2,2-dimethoxyethanamine (3.504 g) and N,N-dimethyl-4-pyridinamine (1.85 g) in triethylamine (8.45 ml) was added to a solution, of intermediate 10 (11.2 g) in 1,4-dioxane (150 ml), while stirring at RT. The reaction mixture was stirred and refluxed for 12 hours. The solvent was evaporated and the residue was taken up in NaOH solution (200 ml; 1 N). This mixture was extracted with $CH_2Cl_2$ (2×100 ml). The organic layer was separated, washed with 1 N NaOH (100 ml), dried (MgSO$_4$), filtered and the solvent was evaporated. The residue was purified by short column chromatography over silica gel (eluent: ethylacetate/($CH_3OH/NH_3$) 97.5/2.5). The desired fractions more collected and the solvent was evaporated, yielding 11.2 g (97%) of (±)-N-[2-[3-(cyclopentyloxy)-4-methoxyphenyl]propyl]-N'-(2,2-dimethoxyethyl)urea (interm. 11).

In a similar way were prepared:
(±)-N-[2-[3-(cyclopentyloxy)-4-methoxyphenyl]-2-methylpropyl]-N'-(2,2-dimethoxyethyl)urea (interm. 12);
N-[[1-[3- (cyclopentyloxy) -4- methoxyphenyl]cyclopropyl]methyl]-N'-(2,2-di-methoxyethyl)urea (interm. 13);
(±)-N-[3-[3-(cyclopentyloxy)-4-methoxyphenyl]butyl]-N'-(2,2-dimethoxyethyl)urea (interm. 14);
(±)-N-[3-[3-(cyclopentyloxy)-4-methoxyphenyl]ethyl]-N'-(2,2-dimethoxyethyl)urea (interm. 15).

EXAMPLE A.7 a) A mixture of 4-(chloromethyl)-2-(cyclopropylmethoxy)-1-methoxybenzene (7.4 g) in DMF (68 ml) was stirred at 60° C. A mixture of potassium cyanide (4.26 g) in water (3.4 ml), previously heated to 80° C., was added dropwise. The resulting reaction mixture was stirred for 30 minutes at 60° C. The reaction mixture was cooled, treated with water (47 ml), and extracted with DIPE. The separated organic layer was dried ($Na_2SO_4$), filtered, and the solvent was evaporated, yielding 6.2 g (85%) of 3-(cyclopropylmethoxy)-4-methoxybenzeneacetonitrile (interm. 16).

b) A mixture of intermediate 16 (5.93 g) in THF (60 ml) was stirred at −78° C. N-lithium-1-methyl-N-(1-methylethyl)ethanamine (1.89 ml; 2 M, in THF) was added dropwise and the resulting reaction mixture was stirred for 30 minutes at −78° C. Methyl iodide (1.89 ml) was added dropwise and the resulting reaction mixture was stirred for 2 hours at RT. The mixture was quenched with a saturated aqueous $Nh_4Cl$ solution and this mixture was extracted with ethylacetate. The separated organic layer was dried ($Na_2SO_4$), filtered, and the solvent was evaporated. The residue was purified by open column chromatography over silica gel (eluent: hexane/ethylacetate 4/1), then by HPLC over silica gel (eluent: hexane/ethylacetate 60/10). The pure fractions were collected and the solvent was evaporated, yielding 3.92 g (62%) of (±)-3-(cyclopropylmethoxy)-4-methoxy-α-methylbenzeneacetonitrile (interm. 17)

c) A mixture of intermediate 17 (3.44 g) in methanol/ammonia (100 ml) was hydrogenated at RT, with Raney nickel (2.5 g) as a catalyst. After uptake of hydrogen, the catalyst was filtered off, and the filtrate was evaporated, yielding 3.6 g (quantitative yield) of (±)-3-(cyclopropylmethoxy)-4methoxy-o-methylbenzeneethanamine (interm. 18).

d) A mixture of intermediate 18 (15 g) and triethylamine (2.88 ml) in $CH_2Cl_2$ (35 ml) was stirred and cooled on an ice-bath. Phenyl chloroformate (2.11 ml) was added dropwise and the resulting reaction mixture was stirred for 3 hours. The reaction mixture was washed with water, then extracted with $CH_2Cl_2$. The separated organic layer was dried ($Na_2SO_4$), filtered, and the solvent was evaporated, yielding 5.56 g (quantitative yield) of (±)-phenyl [2-[3-(cyclopropylmethoxy)-4-methoxyphenyl]-propyl] carbamate (interm. 19).

e) A mixture of 2,2-dimethoxyethylamine (2 ml), triethylamine (4.63 ml) and N,N-dimethyl-4-pyridinamine (1.02 g) in 1.4-dioxane (21 ml) was added dropwise to a solution of intermediate 19 (5.9 g) in 1,4-dioxane (62 ml), and the resulting reaction mixture was stirred and refluxed overnight. The solvent was evaporated and the residue was stirred in NaOH (80 ml; 1N). The mixture was extracted with $CH_2Cl_2$ and the separated organic layer was washed with NaOH (40 ml; 1 N), dried ($Na_2SO_4$), filtered and the solvent evaporated. The residue was purified by column chromatography over silica gel (eluent: $CH_2Cl_2$/2-propanone 90/10 and 80/20). The desired fractions were collected and the solvent was evaporated, yielding 5.01 g (82%) of (±)-N-[2-[3-(cyclopropylmethoxy)-4-methoxyphenyl]propyl]-N'-(2,2-dimethoxyethyl)urea (interm. 20).

EXAMPLE A.8 a) Phenyl lithium (15 ml) was added to a solution of intermediate 21 (3.52 g) in THF (100 ml), stirred at −78° C. and under a $N_2$ flow. The resulting reaction mixture was stirred for 2 hours at −78° C. The mixture was allowed to warm to RT, while stirring for 1 hour. Water (50 ml) was carefully added and the mixture was stirred for 20 minutes, then twice extracted with $CH_3Cl_2$(100 ml). The separated organic layer was dried ($MgSO_4$), filtered, and the solvent was evaporated. The residue was crystallized from ethanol. The precipitate was filtered off, washed with ethanol and diethyl ether, then dried, yielding 1.27 g of 1-[2-(3,4-dimethoxy-phenyl)-2-oxoethyl]-1,3-dihydro-2H-imidazol-2-one (interm. 23)

b) A mixture of intermediate 22 (0.5 g) and potassium carbonate (0.5 g) in ethanol (50 ml) was stirred and refluxed for 30 minutes, then cooled, poured out into water and extracted three times with $CH_2Cl_2$. The organic layer was separated, and the solvent evaporated. The residue was purified by column chromatography over silica gel (eluent: $CH_2Cl_2/CH_3OH$ 95/5). The pure fractions were collected and the solvent was evaporated. The residue was crystallized from $CH_3CN$. The precipitate was filtered off and dried, yielding 1.8 g (41.7%) of 1-[2-(3,4-dimethoxyphenyl)-2-oxoethyl]-2-imidazolidinone (interm. 24; mp. 166.6° C.).

EXAMPLE A.9 a) A mixture of sodium hydride (8.64 g) in THF (700 ml) was stirred at RT under a $N_2$ flow. Diethyl cyanomethylphosphonate (31.86 g) was added dropwise while keeping the temperature below 15° C. The reaction mixture was stirred for 15 minutes. Intermediate 24 (15.84 g) was added portionwise and stirring was continued for 2 hours. The reaction mixture was cooled on an ice-bath, decomposed with an aqueous $NH_4Cl$ solution and this mixture was extracted three times with $CH_2Cl_2$. The separated organic layer was dried ($MgSO_4$), filtered, and the solvent was evaporated. The residue was purified by column chromatography over silica gel (eluent: ethylacetate/$C_2H_5OH$ 99/1). The desired fraction was collected and the solvent was evaporated, the residue was stirred in diisopropyl ether. The precipitate was filtered off and dried, yielding 10.16 g (59%) of (E)-3-(3,4-dimethoxyphenyl)-4-(2-oxo-1-imidazolidinyl)-2-butenenitrile (interm. 25).

EXAMPLE A.10 a) A suspension of 1,1'-carbonyldiimidazole (162.15 g) in $CH_2Cl_2$(500 ml) was stirred on an ice-bath. 2,2-Dimethoxyethanamine (105.14 g) was added dropwise and the resulting reaction solution was stirred for 16 hours. The reaction mixture was cooled on ice, stirred for 30 minutes, and was allowed to crystallize. The precipitate was filtered off, stirred for 15 minutes in ethylacetate (250 ml) at RT, then cooled on an ice-bath for 30 minutes. The precipitate was filtered off, washed twice with DIPE (50 ml), then dried, yielding 137.4 g (69%) of N-(2,2-methoxyethyl)-1H-imidazole-1-carboxamide (interm. 26).

b) A mixture of 5-formyl-2-methoxyphenyl 4-methylbenzenesulfonate (59.1 g) and zinc iodide (3 g) in $CH_2Cl_2$ (250 ml) was stirred at RT. A solution, of trimethylsilanecarbonitrile (25 g) in $CH_2Cl_2$(100 ml) was added dropwise and the resulting reaction mixture was stirred for 2 hours at RT. Water (100 ml) was added and the mixture was stirred for 15 minutes. The layers were separated and the aqueous phase was extracted twice with $CH_2Cl_2$. The separated organic layer was washed twice with water (100 ml), dried ($MgSO_4$), filtered and the solvent evaporated. Toluene was added and azeotroped on the rotary evaporator. The residue was stirred in DIPE, filtered off, and dried, yielding 74 g (94.6%) of (±)-5-[cyano[(trimethylsilyl)oxy]methyl]-2-methoxyphenyl 4-methylbenzenesulfonate (interm 27).

c) (±)-5-[2-amino-1-[(trimethylsilyl)oxy]ethyl]-2-methoxyphenyl-4-methylbenzenesulfonate (interm. 28) was prepared from intermediate 27 according to the procedure described in Example A.7.c.

d) A mixture of intermediate 28 and intermediate 26 (35.8 g) in THF (500 ml) was stirred and refluxed for 4 hours, then stirred overnight at RT. The solvent was evaporated, yielding a quantitative yield of (±)-5-[2-[[[(2,2-dimethoxyethyl)- amino]-carbonyl]amino]-1-[(trimethylsilyl)oxy]ethyl]-2-methoxyphenyl 4-methylbenzenesulfonate (interm. 29).

B. Preparation of the final compounds

EXAMPLE B.1

Hydrochloric acid (88.3 ml: 0.5 N) was added dropwise to a solution of intermediate 11 (11.2 g) in methanol/water (2/1) (150 ml) while stirring at RT. The reaction mixture was stirred for 16 hours, then cooled on an ice-bath. NaOH (44.15 ml; 1 N) was added dropwise and the mixture was stirred for 15 minutes at 0° C. $CH_2Cl_2$ (150 ml) was added and the mixture was allowed to warm to RT. The mixture was extracted with $CH_2Cl_2$(100 ml). The separated organic layer was dried ($MgSO_4$), filtered and the solvent was evaporated. The residue was purified by column chromatography over silica gel (eluent: ethylacetate/($CH_3OH/NH_3$) 97.5/2.5). The desired fractions were collected and the solvent was evaporated. The residue (6 g) was repurified by HPLC over silica gel (eluent: $CH_2Cl_2/CH_3OH$ 94/6) The pure fractions were collected and the solvent was evaporated. The residue was triturated in n-hexane. The precipitate was filtered off, washed with n-hexane and dried, yielding 5.5 g (60%) of (±)-1-[2-[3-(cyclopentyloxy)-4-methoxyphenyl]propyl]-1,3-dihydro-2H-imidazol-2-one (comp. 1).

EXAMPLE B.2

Compound 1 was purified over cellulose triacetate (15–25 μm, 75 cm, diameter: 5 cm, flow: 20 ml/min; eluent: $C_2H_5OH/H_2O$ 95/5). Two desired fraction groups were collected and their solvent was evaporated, giving residue (I) and residue (II). Residue (I) was repurified by short column chromatography over silica gel (eluent: ethylacetate/($CH_3OH/NH_3$)97.5/2.5). The pure fractions were collected and the solvent was evaporated. The residue was dried, yielding (A)-1-[2-[3-(cyclopentyloxy)-4-methoxy-phenyl]propyl]-1,3-dihydro-2H-imidazol-2-one (comp. 6). Residue (II) was repurified by short column chromatography over silica gel (eluent: ethylacetate/ ($CH_3OH/NH_3$) 97.5/2.5). The pure fractions were collected and the solvent was evaporated. The residue was dried, yielding (B)-1-[2-[3-(cyclopentyloxy)-4-methoxyphenyl]propyl]-1,3-dihydro-2H-imidazol-2-one (comp. 7).

EXAMPLE B.3

A mixture of intermediate 2 (1 g) in THF (50 ml) was stirred under a $N_2$ flow at −78° C. Phenyllithium (3.52 ml; 1.8 M solution in cyclohexane/ether 70/30) was added dropwise and the mixture was stirred for 30 minutes at −78° C. The mixture was allowed to warm to RT and stirring was continued for 1 hour. More phenyllithium (1.5 ml) was added dropwise at RT and the mixture was stirred for another 2 hours. The reaction mixture was stirred and refluxed for one hour, then cooled on an ice-bath and quenched with a saturated $NH_4Cl$ solution. This mixture was extracted with $CH_2Cl_2$ (3×100 ml). The separated organic layer was dried over $MgSO_4$, filtered and the solvent was evaporated. The residue was purified by short column chromatography over silica gel (eluent: $CH_2Cl_2/CH_3OH$/($CH_3OH/NH_3$) 90/5/5). The pure fractions were collected and the solvent was evaporated. The residue was triturated in DIPE. The precipitate was filtered off, washed with DIPE and dried, yielding 0.2 g (16%) of (±)-1-[2-[3-(cyclopentyloxy)-4-methoxyphenyl]-2-hydroxy-2-phenylethyl]-1,3-dihydro-2H-imidazol-2-one (comp. 8).

EXAMPLE B.4

A solution of sodium bis(trimethylsilyl)amide in THF (4.14 ml; 2M) was added to a solution of compound 5 (2.5 g) in DMF (25 ml), cooled in an ice-bath, while stirring. The mixture was stirred for another 5 minutes. Ethyl bromoacetate (0.92 ml) was added to one portion, and the resulting reaction mixture was stirred overnight at RT. More sodium bis(trimethylsilyl)amide (2 ml) was added and the reaction mixture was stirred for 3 hours at RT. The reaction mixture was poured out into water/$NH_4Cl$. This mixture was extracted with DIPE and the separated organic layer was dried over $MgSO_4$, filtered and the solvent evaporated, yielding 3.3 g of a syrup containing compound 9. This fraction was purified by column chromatography over silica gel (eluent: $CH_2Cl_2$/($CH_3OH/NH_3$) 100/0, upgrading to 98/2). The desired fractions were collected and the solvent was evaporated. The residue was taken up in ethylacetate and again the solvent was evaporated, yielding 0.7 g of a syrup containing compound 9. This fraction was redissolved in diethyl ether, the solvent was removed and the residue was dried, yielding 0.65 g (20.2%) of (±)-ethyl 3-[1-[3-(cyclopentyloxy)-4-methoxy-phenyl]ethyl]-2,3-dihydro-2-oxo-1H-imidazole-1-acetate (comp. 9).

EXAMPLE B.5 a) HCl (37.82 ml; 0.5 N) was added dropwise to a stirring solution of intermediate 20 (4.62 g) in methanol (48 ml) and water (24.95 ml). The reaction mixture was stirred overnight at RT. The mixture was alkalized with $Na_2CO_3$ and extracted with ethyl-acetate. The separated organic layer was dried ($Na_2SO_4$), filtered, and the solvent was evaporated. The residue was purified by column chromatography over silica gel (eluent: $CH_2Cl_2$/2-propanone 40/10, and $CH_2Cl_2$/ $CH_3OH$ 96/4), then by HPLC over silica gel (eluent: $CH_2Cl_2/CH_3OH$ 97/3). The pure fractions were collected and the solvent was evaporated. The residue was dissolved in $CH_2Cl_2$ and the solvent was evaporated. The residue was stirred up in DIPE for 1 hour, the precipitate was filtered off and dried, yielding 2.66 g (65%) of (±)-1-[2-[3-(cyclopropylmethoxy)-4-methoxyphenyl]propyl]-1,3-dihydro-2H-imidazol-2-one (comp. 10).

b) The procedure described in example B.5.a was repeated yielding 3.66 g of compound 10 which was subsequently optically purified by chiral column chromatography over Chiralpak AS (eluent: hexane/ethanol 70/30). Two pure fractions were collected and the solvent was evaporated, yielding fraction (A) and fraction (B). Each fraction was triturated in DIPE. Each precipitate was filtered off, washed with DIPE, and dried, yielding 0.9 g (14%) of (A)-1-[2-[3-(cyclopropylmethoxy)-4-methoxyphenyl]propyl]-1,3-dihydro-2H-imidazol-2-one (comp. 22) and 0.9 g (14%) of (B)-1-[2-[3-(cyclopropylmethoxy)-4-methoxyphenyl]propyl ]-1,3-dihydro-2H-imidazol-2-one (comp. 23).

EXAMPLE B.6

A mixture of intermediate 21 (1.76 g) and ammonium acetate (5 g) in methanol (100 ml) was hydrogenated at 50° C. with palladium on activated carbon (1g) as a catalyst in the presence of thiophene (4%; 1ml). After uptake of hydrogen, the catalyst was filtered off and the filtrate was evaporated. The residue was taken up into $CH_2Cl_2$. The organic solution was washed with a saturated aqueous $K_2CO_3$ solution (2×100 ml), dried ($MgSO_4$), filtered and the solvent was evaporated. The residue was dissolved in 2-propanol and converted into the hydrochloric acid salt (1:1) with HCl (6 N)/ 2-propanol. The precipitate was filtered off, washed with 2-propanol and DIPE, then dried, yielding 0.5 g (26%) of (±)-1-[2-amino-2-(3,4-dimethoxyphenyl)ethyl]-3-(phenylmethyl)-2-imidazolidinone (comp. 11; mp. 221.7° C.).

EXAMPLE B.7

A solution of intermediate 2 (5 g) in THF (100 ml) was stirred at 10° C. under a $N_2$ flow. Methylmagnesium chloride (15.8 ml) was added dropwise and the resulting reaction mixture was allowed to warm to RT. Stirring was continued for 30 minutes. The mixture was cooled to 0° C. Water (50 ml) was added dropwise and this mixture was extracted with $CH_2Cl_2$ (2×100 ml). The separated organic layer was dried ($MgSO_4$), filtered, and the solvent was evaporated. The separated organic layer was dried ($MgSO_4$), filtered and the solvent was evaporated. The residue was purified by short column chromatography over silica gel (eluent: $CH_2Cl_2$/ $CH_3OH/(CH_3OH/CH_3OH/NH_3)$ 95/2.5/2.5). The desired fractions were collected and the solvent was evaporated. The residue was triturated in ethylacetate. The precipitate was filtered off, washed with ethylacetate, then dried, yielding 1.4 g (26.7%) of (±)-1-[2-[3-(cyclopentyloxy)-4-methoxyphenyl]-2-hydroxypropyl]-1,3-dihydro-2H-imidazol-2-one (comp. 12; mp. 136.2° C.)

EXAMPLE B.8

Sodium borohydride (1.89 g) was added to a suspension of intermediate 24 (5.29 g) in methanol (100 ml). The reaction mixture was stirred at RT for 1 hour. The solvent was evaporated. The residue was taken up in $CH_2Cl_2$ (100 ml). Water (30 ml) was added carefully and the mixture was stirred at RT for 20 minutes. The separated organic layer was dried ($MgSO_4$) filtered and the solvent was evaporated. The residue was crystallized from $CH_3CN$. The precipitate was filtered off, washed with $CH_3CN$ and DIPE, then dried, yielding 1.71 g (32%) of ±)-1-[2-(3,4-dimethoxyphenyl)-2-hydroxy-ethyl]-2-imidazolidinone (comp. 13; mp. 166.4° C.).

EXAMPLE B.9

Acetyl chloride (2.43 g) was added dropwise to a solution of compound 11 (10 g) and triethylamine (3.13 g) in $CH_2Cl_2$ (200 ml), stirred at 0° C. The reaction mixture was stirred overnight at RT. The mixture was washed with water (100 ml). The organic layer was separated. The aqueous phase was extracted with $CH_2Cl_2$ (2×100 ml). The combined organics were dried ($MgSO_4$), filtered and the solvent evaporated. The residue was purified by short column chromatography over silica gel (eluent: $CH_2Cl_2/(CH_3OH/NH_3)$ 98/2). The desired fractions were collected and the solvent was evaporated. The residue was crystallized from ethylacetate. The precipitate was filtered off, washed with ethylacetate and DIPE, then dried, yielding 4.4 g (40%) of (±)-N-[1-(3,4-dimethoxyphenyl)-2-[2-oxo-3-(phenylmethyl)-1-imidazolidinyl]ethyl]acetamide (comp. 14; mp. 156.4° C.).

EXAMPLE B.10

A solution of (±)-1-[2-(3,4-dimethoxyphenyl)-2-ethoxyethyl]-1,3-dihydro-3-(phenylmethyl)-2H-imidazol-2-one (4.86 g) in THF (100 ml) was stirred at RT. Phenyllithium (1.278 g) was added dropwise and the mixture was stirred overnight at RT. The mixture was carefully poured out into ice/water (200 ml), then extracted three times with $CH_2Cl_2$ (150 ml). The separated organic layer was dried ($MgSO_4$), filtered, and the solvent was evaporated. The residue was purified by short column chromatography over silica gel (eluent: $CH_2Cl_2(CH_3OH/NH_3)95/5$). The desired fractions were collected and the solvent was evaporated. The residue was crystallized from ethylacetate. The precipitate was filtered off, washed with ethylacetate and DIPE, then dried, yielding 0.1 g (3%) of (±)-1-[2-(3,4-dimethoxyphenyl)-2-ethoxyethyl]-1,3-dihydro-2H-imidazol-2-one (comp. 15; mp. 133.6° C.).

EXAMPLE B.11

A mixture of compound 14 (4.4 g) in methanol (150 ml) was hydrogenated at 50° C. with palladium on activated carbon (2 g) as a catalyst. After uptake of hydrogen, the catalyst was filtered off and the filtrate was evaporated. The residue was crystallized from $CH_3CN$. The precipitate was filtered off, washed with $CH_3CN$ and DIPE, then dried, yielding 1.71 g (51%) of (±)-N-[1-(3,4-dimethoxyphenyl) [2-(2-oxo-1-imidazolidinyl)-ethyl]acetamide (comp. 16: mp. 169.1° C.).

EXAMPLE B.12

A mixture of intermediate 25 (1.97 g) in methanol (50 ml) was hydrogenated with palladium on activated carbon (1 g) as a catalyst in the presence of thiophene (4%) (1 ml). After uptake of hydrogen, the catalyst was filtered off and the filtrate was evaporated. The residue was purified by HPLC over silica gel (eluent: $CH_2Cl_2/CH_3OH$ 90/10). The pure fractions were collected and the solvent was evaporated. The residue was stirred in DIPE, filtered off and dried. This fraction was recrystallized from ethylacetate. The precipitate was filtered off and dried, yielding 0.96 g (48.7%) of (±)-β-(3,4-dimethoxy-phenyl)-2-oxo-1-imidazolidinebutanenitrile (comp. 17).

EXAMPLE B.13 a) A mixture of intermediate 29 (0.18 mol) and hydrochloric acid (270 ml) in methanol (1000 ml) was stirred for 2 days at RT. The reaction mixture was cooled on an ice-bath. NaOH (270 ml) was added and this mixture was extracted with $CH_2Cl_2$. The separated organic layer was dried ($MgSO_4$), filtered, and the solvent was evaporated. The crude oil was crystallized from DIPE/ethylacetate. The precipitate was filtered off, washed with DIPE, then dried, yielding 32.2 g (44%) of (±)-5-[2-(2,3-dihydro-2-oxo-1H-imidazol-1-yl)-1-hydroxyethyl]-2-methoxyphenyl 4-methylbenzenesulfonate (comp. 18).

b) A mixture of compound 18 (5 g), potassium hydroxide (5.6 g) in methanol (100 ml) was stirred and refluxed for 2 hours. The reaction mixture was treated with acetic acid (8 g). This mixture was diluted with $CH_2Cl_2$ (50 ml), and purified by column chromatography over silica gel (eluent: $CH_2Cl_2/(CH_3OH/NH_3)$ 97/3, upgrading to 90/10). The pure fractions were collected and the solvent was evaporated. The residue was crystallized from $CH_3CN$. The precipitate was filtered off and dried, yielding 1.2 g (38.7%) of (±)-1,3-dihydro-1-[2-hydroxy-2-(3-hydroxy-4-methoxyphenyl) ethyl]-2H-imidazol-2-one (comp. 19).

EXAMPLE B.14

A solution of diethylaminosulfur trifluoride (1.9 g) in $CH_2Cl_2$ (100 ml) was stirred at −78° C. under $N_2$ flow. A solution of (±)-1-[2-[3-(cyclopropylmethoxy)-4-(difluoromethoxy)phenyl]-2-hydroxyethyl]-1,3-dihydro-2H-imidazol-2-one (4 g), prepared according to the procedure described in example B.13.a, in $CH_2Cl_2$ (25 ml) was added dropwise at −78° C., and the resulting reaction mixture was stirred for 4 hours at RT. The mixture was decomposed with water and was extracted with $CH_2Cl_2$. The separated organic layer was dried ($MgSO_4$), filtered, and the solvent was evaporated. The residue was purified by column chromatography over silica gel (eluent: $CH_2Cl_2/CH_3OH$ 97/3). The pure fractions were collected and the solvent was evaporated. The residue was crystallized from DIPE. The precipitate was filtered off, washed with DIPE, then dried, yielding 0.25 g of (±)-1-[2-[3-(cyclopropylmethoxy)-4-(difluoromethoxy)phenyl-2-fluoroethyl]-1,3-dihydro-2H-imidazol-2-one. (comp. 20).

EXAMPLE B.15

A mixture of 1-[[1-(3,4-dimethoxyphenyl)cyclopropyl] methyl]-1,3-dihydro-2H-imidazol-2-one (1.9 g) in DMF (20 ml) was stirred at RT. Sodium hydride (60%) (0.28 g) was added portionwise over 15 minutes. The mixture was stirred for 30 minutes. A solution of bromomethylbenzene (1.45 g) in DMF (5 ml) was added dropwise over 15 minutes. The reaction mixture was stirred for 1 hour. The solvent was evaporated. The residue was purified over silica gel on a glass filter (eluent: $CH_2Cl_2/CH_3OH$ 95/5). The pure fractions were collected and the solvent was evaporated. The residue was crystallized from diethyl ether (20 ml). The precipitate was filtered off and dried, yielding 1.3 g (51%) of 1-[[1-(3,4-dimethoxyphenyl)cyclopropyl]methyl]-1,3-dihydro-3-(phenylmethyl)-2H-imidazol-2-one (comp. 21; mp. 110.5° C.).

The following compounds were prepared according to one of the above examples (Ex. No.).

TABLE 1

| Co. No. | Ex. no. | $R^1$ | $R^2$ | $R^4$ | $R^5$ | Phys. data |
|---|---|---|---|---|---|---|
| 10 | B.5.a | $cC_3H_5$—$CH_2$— | $CH_3$— | $CH_3$— | H | |
| 18 | B.13.a | 4-$CH_3$—$C_6H_4$—$SO_2$— | $CH_3$— | HO— | H | |
| 19 | B.13.b | H— | $CH_3$— | HO— | H | |
| 20 | B.14 | $cC_3H_5$—$CH_2$— | $CHF_2$— | F— | H | |
| 22 | B.5.b | $cC_3H_5$—$CH_2$— | $CH_3$— | $CH_3$— | H | (A) |
| 23 | B.5.b | $cC_3H_5$—$CH_2$— | $CH_3$— | $CH_3$— | H | (B) |
| 24 | B.13.b | H— | $CH_3$— | $CH_3$— | H | |
| 25 | B.13.b | H— | $CH_3$— | $CH_3$—O— | H | |
| 26 | B.13.a | $cC_3H_5$—$CH_2$— | $CHF_2$— | HO— | H | |
| 27 | B.13.a | $cC_3H_5$—$CH_2$— | $CH_3$— | HO— | H | |
| 28 | B.1 | $cC_3H_5$—$CH_2$— | $CHF_2$— | $CH_3$— | H | |
| 29 | B.1 | 3-tetrahydrofuranyl | $CH_3$— | $CH_3$— | H | |
| 30 | B.1 | $cC_5H_9$— | $CF_3$— | $CH_3$— | H | |
| 31 | B.1 | $cC_6H_{11}$—$CH_2$— | $CH_3$— | $CH_3$— | H | |
| 32 | B.1 | $cC_5H_9$—$CH_2$— | $CH_3$— | $CH_3$— | H | |
| 33 | B.1 | 2-tetrahydrofuranyl-$CH_2$— | $CH_3$— | $CH_3$— | H | |
| 34 | B.1 | $C_6H_5$—$CH_2$— | $CHF_2$— | $CH_3$— | H | |
| 35 | B.1 | 3-tetrahydrofuranyl | $CH_3$— | H | H | |
| 36 | B.1 | bicyclo[2.2.1]-heptanyl | $CH_3$— | $CH_3$— | H | 89.4° C. |
| 37 | B.1 | $cC_5H_9$— | $CHF_2$— | $CH_3$— | H | 80.6° C. |
| 38 | B.1 | $CHF_2$— | $CHF_2$— | $CH_3$— | H | 90.1° C. |
| 39 | B.1 | 4-$CH_3$—$C_6H_4$—$SO_2$— | $CH_3$— | $CH_3$— | H | |
| 40 | B.14 | 4-$CH_3$—$C_6H_4$—$SO_2$— | $CH_3$— | F— | H | |
| 41 | B.14 | $cC_3H_5$—$CH_2$— | $CH_3$— | F— | H | |

TABLE 2

| Co. no. | Ex. no. | $R^4$ | $R^5$ | A—B | L | Phys. data |
|---|---|---|---|---|---|---|
| 11 | B.6 | $NH_2$ | H | $CH_2$—$CH_2$ | $C_6H_5$—$CH_2$— | 221.7° C. |
| 13 | B.8 | —OH | H | $CH_2$—$CH_2$ | H | 166.4° C. |
| 14 | B.9 | $CH_3$—C(=O)—NH— | H | $CH_2$—$CH_2$ | $C_6H_5$—$CH_2$— | 156.4° C. |
| 15 | B.10 | $C_2H_5$—O— | H | CH=CH | H | 133.6° C. |
| 16 | B.11 | $CH_3$—C(=O)—NH— | H | $CH_2$—$CH_2$ | H | 169.1° C. |
| 17 | B.12 | NC—$CH_2$— | H | $CH_2$—$CH_2$ | H | |
| 42 | B.1 | $C_6H_5$—$CH_2$— | H | CH=CH | H | |
| 43 | B.1 | $C_6H_5$—$C_2H_4$— | H | CH=CH | H | |
| 44 | B.1 | 3-pyridinyl-$CH_2$— | H | CH=CH | H | 130.5° C. |
| 45 | B.1 | $CF_3$— | H | CH=CH | H | 166.5° C. |
| 46 | B.1 | $C_4H_9$— | H | CH=CH | H | 93.9° C. |
| 47 | B.1 | $cC_6H_{11}$— | H | CH=CH | H | 188.5° C. |
| 48 | B.1 | $(CH_3)_2CH$— | H | CH=CH | H | 119.1° C. |
| 49 | B.1 | $(CH_3)_2CH$—$CH_2$— | H | CH=CH | H | 129.2° C. |

TABLE 2-continued

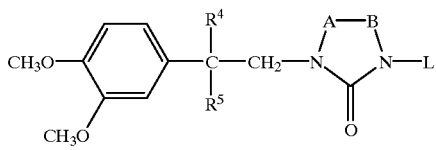

| Co. no. | Ex. no. | R⁴ | R⁵ | A—B | L | Phys. data |
|---|---|---|---|---|---|---|
| 50 | B.1 | C₂H₅— | H | CH=CH | H | 124.6° C. |
| 51 | B.2 | C₆H₅— | OH | CH=CH | H | 171.2° C. |
| 52 | B.2 | C₆H₅— | OH | CH₂—CH₂ | H | 154.4° C. |
| 53 | B.15 | CH₃— | H | CH=CH | C₆H₅—CH₂— | 59.2° C. |
| 54 | B.15 | CH₃— | H | CH=CH | CH₂=CH—CH₂— | |
| 55 | B.15 | CH₃— | H | CH=CH | C₄H₉— | |
| 56 | B.15 | CH₃— | H | CH=CH | C₂H₅—O—C(=O)—C₃H₆— | |
| 57 | B.15 | CH₃— | H | CH=CH | C₆H₅—CH=CH—CH₂— | |
| 58 | B.15 | C₂H₅—O— | H | CH=CH | C₆H₅—CH₂ | 90.8° C. |
| 59 | B.8 | —OH | H | CH₂—CH₂ | C₂H₅—O—C(=O)— | 104.8° C. |
| 60 | B.8 | —OH | H | CH=CH | C₆H₅—CH₂— | 114.4° C. |

TABLE 3

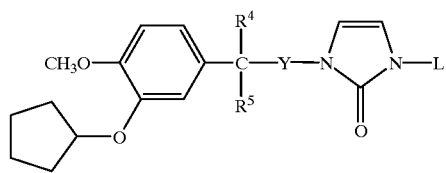

| Co. no. | Ex. no. | Y | R⁴ | R⁵ | L | Phys. data |
|---|---|---|---|---|---|---|
| 1 | B.1 | CH₂ | CH₃— | H | H | 87.7° C. |
| 2 | B.1 | CH₂ | CH₃— | CH₃— | H | 144.7° C. |
| 4 | B.1 | C₂H₄ | CH₃— | H | H | 96.6° C. |
| 5 | B.1 | direct bond | CH₃— | H | H | 98.2° C. |
| 6 | B.2 | CH₂ | CH₃— | H | H | (A); 104.0° C. |
| 7 | B.2 | CH₂ | CH₃— | H | H | (B); 108.1° C. |
| 8 | B.3 | CH₂ | C₆H₅— | HO— | H | 119.9° C. |
| 9 | B.4 | direct bond | CH₃— | H | C₂H₅—O—C(=O)—CH₂— | |
| 12 | B.7 | CH₂ | HO— | CH₃— | H | 136.2° C. |
| 61 | B.14 | CH₂ | CH₃— | F— | H | |
| 62 | B.14 | CH₂ | F— | H | H | |
| 63 | B.13.a | CH₂ | HO— | H | H | 98.8° C. |
| 64 | B.1 | CH(CH₃) | CH₃— | H | H | |
| 65 | B.1 | CH₂ | H— | H | H | 133.6° C. |

TABLE 4

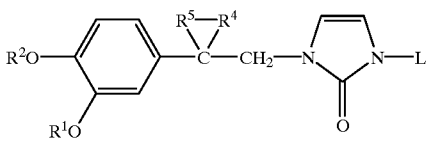

| Co. no. | Ex. no. | R¹ | R² | R⁴—R⁵ | L | Phys. data |
|---|---|---|---|---|---|---|
| 3 | B.1 | cC₅H₉— | CH₃ | —CH₂—CH₂— | H | 114.2° C. |
| 21 | B.15 | CH₃ | CH₃ | —CH₂—CH₂— | C₆H₅—CH₂— | 110.5° C. |
| 66 | B.15 | CH₃ | CH₃ | —CH₂—CH₂— | CH₂=CH—CH₂— | 93.8° C. |
| 67 | B.15 | CH₃ | CH₃ | —CH₂—CH₂— | C₄H₉— | |

TABLE 4-continued

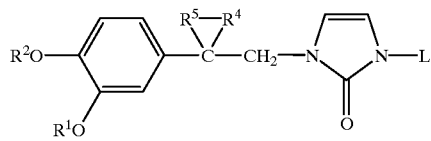

| Co. no. | Ex. no. | $R^1$ | $R^2$ | $R^4$—$R^5$ | L | Phys. data |
|---|---|---|---|---|---|---|
| 68 | B.1 | $cC_5H_9$— | $CH_3$ | —$C_2H_4$—O—$C_2H_4$— | H | 172.5° C. |
| 69 | B.1 | $cC_5H_9$— | $CH_3$ | —$C_5H_{10}$— | H | 192.4° C. |
| 70 | B.1 | $cC_5H_9$— | $CHF_2$ | —$CH_2$—$CH_2$— | H | |
| 71 | B.1 | $cC_5H_9$— | $CH_3$ | —$C_4H_8$— | H | 207.3° C. |
| 72 | B.1 | $cC_5H_9$— | $CH_3$ | —$C_3H_6$— | H | 187.2° C. |
| 73 | B.15 | $CH_3$ | $CH_3$ | —$CH_2$—$CH_2$— | $C_2H_5$—O—C(=O)—$C_3H_6$— | |
| 74 | B.1 | $CH_3$ | $CH_3$ | —$CH_2$—$CH_2$— | H | 147.3° C. |
| 75 | B.15 | $CH_3$ | $CH_3$ | —$CH_2$—$CH_2$— | 4-$NO_2$—$C_6H_4$—$CH_2$— | |

C. Pharmacological example

The PDE IV inhibitory activity, both in vitro and in vivo, of the compounds of formula (I), including the compounds 1,3-dihydro-1-[2-(3,4-dimethoxyphenyl)propyl]-2H-imidazol-2-one (comp. 76); 1,3-dihydro-1-[2-(3,4-dimethoxyphenyl)propyl]-5-methyl-2H-imidazol-2-one (comp. 77); 1-[2-(3,4-dimethoxyphenyl)ethyl]-1,3,4,5-tetrahydro-2H-imidazol-2-one (comp. 78); 1,3-dihydro-1-[2-(3,4-dimethoxyphenyl)ethyl]-2H-imidazol-2-one (comp. 79); 1-[2-(3,4-dimethoxyphenyl)propyl]-1,3,4,5-tetrahydro-2H-imidazol-2-one (comp. 80); 1,3-dihydro-2-[2-(2-bromo-4,5-dimethoxyphenyl)ethyl]-2H-imidazol-2-one (comp. 81); 1-[2-(3,4-dimethoxyphenyl)ethyl]-1,3-dihydro-2H-imidazol-2-one (comp. 82); 1,3-dihydro-1-[2-(3,4-dimethoxyphenyl)-2-methoxy-ethyl]-2H-imidazol-2-one (comp. 83); 1,3-dihydro-1-[(3,4-dimethoxyphenyl)methyl]-2H-imidazol-2-one (comp. 84); 1,3-dihydro-1-[3-(3,4-dimethoxyphenyl)propyl]-2H-imidazol-2-one (comp. 85); and 1,3-dihydro-1-[2-(3,4-dimethoxyphenyl)ethyl]-2-methyl-3H-imidazol-2-one (comp. 86); is demonstrated by means of the following two examples.

EXAMPLE C.1

Inhibition of recombinant human mononuclear lymphoctye (MNL) phosphodiesterase type IV B produced in insect cells with a baculovirus vector The alleviating and/or curing effect of the instant compounds on allergic and atopic diseases was assessed by an in vitro assay system to detect an inhibiting effect on the recombinant human MNL phosphodiesterase type IV B.

Seventy-two hours after infection with recombinant baculovirus, the insect cells were harvested and pelleted at 500 g for 5 minutes. The cells were lysed in 10 ml lysis-buffer consisting of 20 mM Tris, 10 mM EGTA, 2 mM $Na_2EDTA$, 1% Triton-X-100, 1 mM $Na_3VO_4$, 10 mM NaF, 2 μg/ml of leupeptine, pepstatine and aprotinine, 0.3 μg/ml benzamidine and 100 μg/ml TPCK pH 7.5. After 5 minutes on ice, solubilized cells were centrifuged at 4000 rpm for 15 minutes at 4° C. The resulting supernatant was filtered through a 0.45 μm filter (Millipore) and brought to TBS buffer (50 mM Tris, 150 mM NaCl pH 7.4).

The supernatant containing phosphodiesterase (PDE) type IV B, was subsequently loaded onto a 5 ml anti-FLAG-$M_2$ affinity gel column, previously activated with 5 ml 100 mM glycine pH 3.5 and equilibrated with 20 ml 50 mM Tris, 150 mM NaCl pH 7.4. After washing the column with equilibration buffer, PDE IV was eluted in 1.5 ml fractions containing 37.5 μl 1M Tris pH 8. The fractions were dialyzed overnight against 20 mM Tris, 2 mM $Na_2EDTA$ and 400 mM NaCl pH 7.5 and tested for PDE IV activity. Identification was done on SDS PAGE and Western Blot (anti-FLAG-$M_2$). Active fractions were pooled, brought to 10% glycerol and stored at −70° C.

The incubation mixture (pH 8) (200 μl) contained 20 mM Tris, 10 mM magnesium sulphate, 0.8 μM $^3$H-cAMP (310 mCi/mmole) and the phosphodiesterase type IV, the amount depending on the enzymatic activity. A protein concentration was chosen that showed a linear increase of phosphodiesterase activity during an incubation period of maximum 10 minutes at 37° C. and where less than 10% of the initial substrate was hydrolyzed.

When the effect of different compounds on phosphodiesterase activity was tested, the medium without cAMP was incubated with the compound(s) or its carrier (DMSO-1% final concentration) for 5 min. The enzymatic reaction was started by addition of $^3$H-cAMP and stopped 10 min later after transferring the microtiter-plate in a waterbath at 100° C. for 5 min. After cooling to room temperature, alkaline phosphatase (0.25 μg/ml) was added and the mixture was incubated at 37° C. for 20 min. 100 μl of the mixture was subsequently applied to a GF-B filter-microtiter-plate (Millipore) filled with 300 μl DEAE-Sephadex-A25 suspension. The plate was washed 3 times with 75 μl 20 mM Tris pH 7.5 and the filtrates were collected for counting in the Packard Top Count scintillation counter.

The inhibiting effect of the present compounds on recombinant human MNL phosphodiesterase PDE IV B was measured at different concentrations of the instant compounds. The $IC_{50}$ values (expressed in M) were calculated graphically from the thus obtained inhibition values. Table 5 shows available $IC_{50}$ values of the present compounds on recombinant human MNL PDE IV B.

TABLE 5

| Comp. No. | $IC_{50}$ (in M) |
|---|---|
| 1 | $4.8 \times 10^{-9}$ |
| 2 | $5.2 \times 10^{-8}$ |
| 3 | $7.5 \times 10^{-9}$ |
| 4 | $5.5 \times 10^{-7}$ |
| 5 | $1.5 \times 10^{-7}$ |
| 6 | $4.1 \times 10^{-9}$ |
| 7 | $4.3 \times 10^{-8}$ |
| 8 | $1.9 \times 10^{-6}$ |
| 10 | $<1 \times 10^{-8}$ |
| 12 | $2.9 \times 10^{-7}$ |
| 22 | $4.5 \times 10^{-8}$ |
| 29 | $2.4 \times 10^{-7}$ |
| 32 | $1.4 \times 10^{-7}$ |
| 33 | $2.3 \times 10^{-6}$ |
| 34 | $1.9 \times 10^{-7}$ |
| 35 | $1.8 \times 10^{-7}$ |
| 36 | $3.9 \times 10^{-8}$ |
| 37 | $7.0 \times 10^{-10}$ |
| 38 | $2.0 \times 10^{-8}$ |
| 61 | $5.9 \times 10^{-8}$ |
| 62 | $1.7 \times 10^{-8}$ |
| 63 | $4.0 \times 10^{-8}$ |
| 64 | $2.6 \times 10^{-7}$ |
| 65 | $6.8 \times 10^{-9}$ |
| 70 | $4.9 \times 10^{-8}$ |
| 71 | $6.9 \times 10^{-7}$ |
| 72 | $5.4 \times 10^{-8}$ |
| 74 | $2.9 \times 10^{-7}$ |
| 76 | $1.5 \times 10^{-7}$ |
| 77 | $7.3 \times 10^{-6}$ |
| 78 | $9.0 \times 10^{-6}$ |
| 79 | $7.7 \times 10^{-7}$ |
| 80 | $3.2 \times 10^{-6}$ |
| 82 | $4.6 \times 10^{-7}$ |
| 83 | $2.7 \times 10^{-6}$ |
| 86 | $1.8 \times 10^{-6}$ |

EXAMPLE C.2

Dextran-induced oedema formation in mouse ear

Systemic injection of dextran T500 in normal, non-sensitized mice elicits increased vascular permeability, leading to extravasation and oedema of the extremities. When dextran is injected together with a blue dye, blueing of the ears is the most prominent feature of oedematous response.

Male Swiss mice weighting 24–26 g were orally pre-treated with the test compound dissolved in PEG-200 at different concentrations or solvent. One hour later, the mice were given an intravenous injection with an isotonic saline solution containing 12 mg/ml dextran T500 and 2.6 mg/ml pontamine sky-blue dye, in a volume of 0.1 ml per 10 g body weight. One hour and forty-five minutes later, the animals are sacrificed by ether and their ears removed. Extraction and quantification of the extravasated dye is done as described by Van Wauwe and Goossens (Drug Dev. Res. 1986, 8, 213–218).

The extravasation of the dye is characterized by the blueing value which is defined as the concentration of the extracted dye in both ears. The background blueing value was determined once as the mean blueing value obtained by injecting a group of mice with a saline solution containing only dextran T500 and the blue dye. Table 6 lists the percentage inhibition of the extravasation of the dye when compared with the background extravasation of the dye when the test compound was administered at a dose of 5 mg/kg. The test compounds indicated by an asterisk (*) were tested at a dose of 2.5 mg/kg

TABLE 6

| Comp. No. | % inhibition |
|---|---|
| 1 | 83.1 |
| 2 | 34.0 |
| 3 | 34.7 |
| 4 | 10.9 |
| 5 | 35.1 |
| 6 | 85.1 |
| 7 | 67.0 |
| 8 | 12.4 |
| 9 | 10.2 |
| 10 | 91.9 |
| 11 | 26.8 |
| 12 | 87.5 |
| 13 | 36.3 |
| 14 | 32.3 |
| 16 | 10.8 |
| 19* | 49.4 |
| 20* | 94.4 |
| 22 | 83.5 |
| 23 | 72.1 |
| 24* | 26.8 |
| 26* | 67.6 |
| 27* | 90.7 |
| 28 | 86.1 |
| 29* | 90.7 |
| 30 | 44.9 |
| 31* | 50.4 |
| 32 | 76.2 |
| 33 | 65.8 |
| 34 | 31.1 |
| 35 | 90.1 |
| 36 | 97.7 |
| 37 | 75.7 |
| 38 | 76.6 |
| 41* | 99.6 |
| 43 | 13.1 |
| 44 | 12.0 |
| 45 | 47.4 |
| 46 | 14.8 |
| 47 | 23.0 |
| 48 | 35.4 |
| 50 | 34.4 |
| 51 | 14.8 |
| 53 | 37.6 |
| 54 | 42.5 |
| 57 | 30.0 |
| 59 | 51.7 |
| 61 | 90.4 |
| 62 | 100 |
| 63 | 69.3 |
| 64 | 41.3 |
| 65 | 63.7 |
| 67 | 9.8 |
| 69 | 3.7 |
| 70 | 43.6 |
| 71 | 26.0 |
| 72 | 6.0 |
| 76 | 69.0 |
| 77 | 35.8 |
| 78 | 31.3 |
| 79 | 61.6 |
| 80 | 53.4 |
| 81 | 34.1 |
| 82 | 28.2 |
| 83 | 18.6 |
| 84 | 46.5 |
| 85 | 31.6 |
| 86 | 39.0 |

D. Composition examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

EXAMPLE D.1 film-coated tablets

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10,000 tablets, each comprising 1'0 mg of the active ingredient.

Coating

To a solution of 10 g methyl cellulose in 75 ml of denaturated ethanol there was added a solution of 5 g of ethyl cellulose in 150 ml of dichloromethane. Then there were added 75 ml of dichloromethane and 2.5 ml 1,2,3-propenetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

EXAMPLE D.2

2% cream 75 mg stearyl alcohol, 2 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70 to 75° C. while using a homogenizer for liquids. The resulting emulsion is allowed to cool to below 25° C. while continuously mixing. A solution of 20 mg A.I., 1 mg polysorbate 80 and purified water and a solution of 2 mg sodium sulfite anhydrous in purified water are next added to the emulsion while continuously mixing. The cream, 1 g of the A.I. is homogenized and filled into suitable tubes.

EXAMPLE D.3

2% topical gel

To a solution of 200 mg hydroxypropyl β-cyclodextrine in purified water is added 20 mg of A.I. while stirring. Hydrochloric acid is added until complete dissolution and the sodium hydroxide is added until pH 6.0. This solution is added to a dispersion of 10 mg carrageenan PJ in 50 mg propylene glycol while mixing. While mixing slowly, the mixture is heated to 50° C. and allowed to cool to about 35° C. whereupon 50 mg ethyl alcohol 95% (v/v) is added. The rest of the purified water q.s. ad 1 g is added and the mixture is mixed to homogenous.

EXAMPLE D.4

2% topical cream

To a solution of 200 mg hydroxypropyl β-cyclodextrine in purified water is added 20 mg of A.I. while stirring. Hydrochloric acid is added until complete dissolution and next sodium hydroxide is added until pH 6.0. While stirring, 50 mg glycerol and 35 mg polysorbate 60 are added and the mixture is heated to 70° C. The resulting mixture is added to a mixture of 100 mg mineral oil, 20 mg stearyl alcohol, 20 mg cetyl alcohol, 20 mg glycerol monostearate and 15 mg sorbate 60 having a temperature of 70° C. while mixing slowly. After cooling down to below 25° C., the rest of the purified water q.s. ad 1 g is added and the mixture is mixed to homogenous.

EXAMPLE D.5

2% liposome formulation

A mixture of 10 g phosphatidyl choline and 1 g cholesterol in 7.5 g ethyl alcohol is stirred and heated at 40° C. until complete dissolution. 2 g A.I. microfine is dissolved in purified water by mixing while heating at 40° C. The alcoholic solution is added slowly to the aqueous solution while homogenizing during 10 minutes. 1.5 g Hydroxypropyl-methylcellulose in purified water is added while mixing until swelling is complete. The resulting solution is adjusted to pH 5.0 with sodium hydroxide 1 N and diluted with the rest of the purified water ad 100 g.

What is claimed is:

1. A compound of the formula (I)

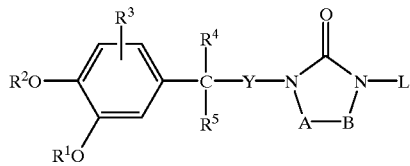

a N-oxide form, a pharmaceutically acceptable acid or base addition salt or a stereochemically isomeric form thereof, wherein:

$R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

$R^3$ is hydrogen, halo or $C_{1-6}$alkyloxy;

$R^4$ is hydrogen; halo; $C_{1-6}$alkyl; trifluoromethyl; $C_{3-6}$cycloalkyl; carboxyl; $C_{1-4}$alkyloxycarbonyl; $C_{3-6}$-cycloalkylaminocarbonyl; aryl; Het$^1$; or $C_{1-6}$alkyl substituted with cyano, amino, hydroxy, $C_{1-4}$alkylcarbonylamino, aryl or Het$^1$; or $R^4$ is a radical of formula:

—O—$R^6$  (a-1); or

—NH—$R^7$  (a-2);

wherein $R^6$ is hydrogen; $C_{1-6}$alkyl; $C_{1-6}$alkyl substituted with hydroxy, carboxyl, $C_{1-4}$alkyloxycarbonyl, amino, mono- or di($C_{1-4}$alkyl)amino, Het$^1$ or aryl;

$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, Het$^1$ or aryl;

43

$R^5$ is hydrogen, halo, hydroxy or $C_{1-6}$alkyl; or $R^4$ $R^5$ taken together may form a bivalent radical of formula:

$$-(CH_2)_n- \quad (b-1);$$

$$-CH_2-CH_2-O-CH_2-CH_2- \quad (b-2);$$

$$-CH_2-CH_2-N(R^8)-CH_2-CH_2- \quad (b-3); \text{ or}$$

$$-CH_2-CH=CH-CH_2- \quad (b-4);$$

wherein n is 2, 3, 4 or 5;

$R^8$ is hydrogen, $C_{1-6}$alkyl, $C_{1-6}$alkylsulfonyl or p-toluenesulfonyl;

Y is a direct bond, halo$C_{1-4}$alkanediyl or $C_{1-4}$alkanediyl;

-A-B- is a bivalent radical of formula:

$$-CR^9=CR^{10}- \quad (c-1); \text{ or}$$

$$-CHR^9-CHR^{10}- \quad (c-2);$$

wherein each $R^9$ and $R^{10}$ independently is hydrogen or $C_{1-4}$alkyl; and L is hydrogen; $C_{1-6}$alkyl; $C_{1-6}$alkylcarbonyl; $C_{1-6}$alkyloxycarbonyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and $Het^2$; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, hydroxy, $C_{1-4}$alkyl, $C_{1-4}$alkyloxy, $C_{1-4}$alkyloxycarbonyl and $C_{1-4}$alkylcarbonylamino;

$Het^1$ is pyridinyl; pyridinyl substituted with $C_{1-4}$alkyl; furanyl; furanyl substituted with $C_{1-4}$alkyl; thienyl; thienyl substituted with $C_{1-4}$alkylcarbonylamino; hydroxypyridinyl, hydroxypyridinyl substituted with $C_{1-4}$alkyl or $C_{1-4}$alkoxy$C_{1-4}$alkyl; imidazolyl; imidazolyl substituted with $C_{1-4}$alkyl; thiazolyl; thiazolyl substituted with $C_{1-4}$alkyl; oxazolyl; oxazolyl substituted with $C_{1-4}$alkyl; isoquinolinyl; isoquinolinyl substituted with $C_{1-4}$alkyl; quinolinonyl, quinolinonyl substituted with $C_{1-4}$alkyl; morpholinyl; piperidinyl; piperidinyl substituted with $C_{1-4}$alkyl, $C_{1-4}$alkyloxycarbonyl or aryl$C_{1-4}$alkyl; piperazinyl; piperazinyl substituted with $C_{1-4}$alkyl, $C_{1-4}$alkyloxycarbonyl or aryl$C_{1-4}$alkyl; and $Het^2$ is morpholinyl; piperidinyl; piperidinyl substituted with $C_{1-4}$alkyl or aryl$C_{1-4}$alkyl; piperazinyl; piperazinyl substituted with $C_{1-4}$alkyl or aryl$C_{1-4}$alkyl; pyridinyl; pyridinyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino, provided that the compound is other than:
  1,3-dihydro-1-[2-(3,4-dimethoxyphenyl)propyl]-2H-imidazol-2-one;
  1,3-dihydro-1-[2-(3,4-dimethoxyphenyl)propyl]-5-methyl-2H-imidazol-2-one;
  1-[2-(3,4-dimethoxyphenyl)ethyl]-1,3,4,5-tetrahydro-2H-imidazol-2-one;
  1,3-dihydro-1-[2-(3,4-dimethoxyphenyl)ethyl]-2H-imidazol-2-one;
  1-[2-(3,4-dimethoxyphenyl)propyl]-1,3,4,5-tetrahydro-2H-imidazol-2-one;
  1-[2-(3,4-diethoxyphenyl)ethyl]-1,3-dihydro-2H-imidazol-2-one;

44

1,3-bis[2-(3,4-dimethoxyphenyl)ethyl]-1,3,4,5-tetrahydro-2H-imidazol-2-one; or
  1-[2-(3,4-dimethoxyphenyl)ethyl]-3-phenylmethyl-1,3,4,5-tetrahydro-2H-imidazol-2-one.

2. A compound according to claim 1 wherein $R^1$ and $R^2$ each independently are hydrogen, $C_{1-6}$alkyl, difluoromethyl, trifluoromethyl, $C_{3-6}$cycloalkyl, bicyclo[2.2.1]-2-heptenyl or $C_{1-10}$alkyl substituted with one or two substituents each independently selected from $C_{3-7}$cycloalkyl and a saturated 5-, 6- and 7-membered heterocycle containing one or two heteroatoms selected from oxygen, sulfur or nitrogen; and L is hydrogen; $C_{1-6}$alkyl; $C_{1-6}$alkyl substituted with hydroxy, $C_{1-4}$alkyloxy, $C_{1-4}$alkyloxycarbonyl, mono- or di($C_{1-4}$alkyl)amino, aryl or $Het^2$; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, $C_{1-4}$alkyl, $C_{1-4}$alkyloxy, $C_{3-6}$cycloalkyl, trifluoromethyl, amino and $C_{1-4}$alkylcarbonylamino.

3. A compound according to claim 2, wherein $R^1$ and $R^2$ each independently are hydrogen, $C_{1-6}$alkyl, difluoromethyl, trifluoromethyl, $C_{3-6}$cycloalkyl or bicyclo[2.2.1]-2-heptenyl;

$R^4$ is hydrogen; $C_{1-6}$alkyl; trifluoromethyl; $C_{3-6}$cycloalkyl; carboxyl; $C_{1-4}$alkyloxycarbonyl; $C_{3-6}$-cycloalkylaminocarbonyl; aryl; $Het^1$; or $C_{1-6}$alkyl substituted with cyano, amino, hydroxy, $C_{1-4}$alkylcarbonylamino, aryl or $Het^1$; or $R^4$ is a radical of formula:

$$-O-R^6 \quad (a-1); \text{ or}$$

$$-NH-R^7 \quad (a-2);$$

wherein $R^6$ is hydrogen; $C_{1-6}$alkyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^5$ is hydrogen, hydroxy or $C_{1-6}$alkyl; or $R^4$ $R^5$ taken together form a bivalent radical of formula:

$$-(CH_2)_n- \quad (b-1);$$

$$-CH_2-CH_2-O-CH_2-CH_2- \quad (b-2);$$

$$-CH_2-CH_2-N(R^8)-CH_2-CH_2- \quad (b-3); \text{ or}$$

$$-CH_2-CH=CH-CH_2- \quad (b-4);$$

wherein n is 2, 3, 4 or 5;

$R^8$ is hydrogen, $C_{1-6}$alkyl, $C_{1-6}$alkylsulfonyl or p-toluenesulfonyl;

Y is a direct bond, or $C_{1-4}$alkanediyl;

-A-B- is a bivalent radical of formula:

$$-CR^9=CR^{10}- \quad (c-1); \text{ or}$$

$$-CHR^9-CHR^{10}- \quad (c-2);$$

wherein each $R^9$ and $R^{10}$ independently is hydrogen or $C_{1-4}$alkyl; and L is hydrogen; $C_{1-6}$alkyl; $C_{1-6}$alkyl substituted with hydroxy, $C_{1-4}$alkyloxy, $C_{1-4}$alkyloxycarbonyl, mono- or di($C_{1-4}$alkyl)amino, aryl or Het²; $C_{3-6}$alkenyl; $C_{3-6}$alkenyl substituted with aryl; piperidinyl; piperidinyl substituted with $C_{1-4}$alkyl or aryl $C_{1-4}$alkyl; $C_{1-6}$alkylsulfonyl or arylsulfonyl;

aryl is phenyl or phenyl substituted with one, two or three substituents selected from halo, $C_{1-4}$alkyl, $C_{1-4}$alkyloxy, $C_{3-6}$cycloalkyl, trifluoromethyl, amino and $C_{1-4}$alkylcarbonylamino.

4. A compound according to claim 1 wherein $R^4$ is halo; trifluoromethyl; $C_{3-6}$cycloalkyl; $C_{3-6}$cycloalkylaminocarbonyl; aryl; Het¹; or $C_{1-6}$alkyl substituted with cyano, amino, hydroxy, $C_{1-4}$alkylcarbonylamino, aryl or Het¹; or $R^4$ is a radical of formula:

  (a-1); or

  (a-2);

wherein $R^6$ is $C_{1-6}$alkyl substituted with hydroxy, carboxyl, $C_{1-4}$alkyloxycarbonyl, amino, mono- or di($C_{1-4}$alkyl)amino, Het¹ or aryl;

$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, Het¹ or aryl; or $R^5$ is halo; or $R^4$ and $R^5$ taken together form a bivalent radical of formula:

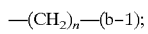

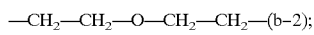

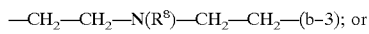

wherein n is 2, 3, 4 or 5;

$R^8$ is hydrogen, $C_{1-6}$alkyl, $C_{1-6}$alkylsulfonyl or p-toluenesulfonyl.

5. A compound according to claim 1 wherein $R^1$ is hydrogen; $C_{3-6}$cycloalkyl wherein one or two carbon atoms are replaced by a heteroatom selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen.

6. A compound according to claim 1 wherein $R^4$ is halo; $C_{3-6}$cycloalkyl; $C_{3-6}$cycloalkylaminocarbonyl; aryl; Het¹; or $C_{1-6}$alkyl substituted with amino, $C_{1-6}$alkylcarbonylamino, aryl or Het¹; or $R^4$ is a radical of formula:

  (a-1); or

  (a-2);

wherein $R^6$ is $C_{1-6}$alkyl; $C_{1-6}$alkyl substituted with hydroxy, carboxyl, $C_{1-4}$alkyloxycarbonyl, amino, mono- or di($C_{1-4}$alkyl)amino, Het¹ or aryl;

$R^7$ is hydrogen; $C_{1-6}$alkyl; $C_{1-6}$alkylcarbonyl; $C_{1-6}$alkyl substituted with hydroxy, carboxyl, $C_{1-4}$alkyloxycarbonyl, amino, mono- or di($C_{1-4}$alkyl)amino, Het¹ or aryl; or $R^5$ is halo; or $R^4$ and $R^5$ taken together form a bivalent radical of formula:

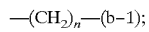

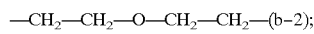

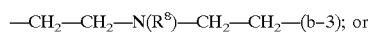

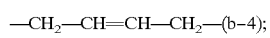

wherein n is 2, 3, 4 or 5;

$R^8$ is hydrogen, $C_{1-6}$alkyl, $C_{1-6}$alkylsulfonyl or p-toluenesulfonyl.

7. A compound according to claim 1 wherein $R^1$ is hydrogen; $C_{1-6}$alkyl; difluoromethyl; trifluoromethyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

8. A compound according to claim 1 wherein $R^4$ is $C_{1-6}$alkyl; trifluoromethyl; $C_{3-6}$cycloalkyl; carboxyl; $C_{1-4}$alkyloxycarbonyl; $C_{3-6}$cycloalkylaminocarbonyl; or $C_{1-6}$alkyl substituted with cyano, amino, hydroxy, $C_{1-4}$alkylcarbonylamino; or $R^4$ is a radical of formula:

  (a-1); or

  (a-2);

wherein $R^6$ is $C_{1-6}$alkyl substituted with carboxyl, $C_{1-4}$alkyloxycarbonyl, amino, mono- or di($C_{1-4}$alkyl)amino, Het¹ or aryl;

$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, Het¹ or aryl; or $R^5$ is $C_{1-6}$alkyl; or $R^4$ and $R^5$ taken together form a bivalent radical of formula:

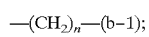

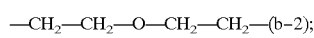

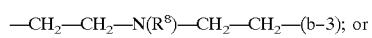

wherein n is 2, 3, 4 or 5;

$R^8$ is hydrogen, $C_{1-6}$alkyl, $C_{1-6}$alkylsulfonyl or p-toluenesulfonyl.

9. A compound according to claim 1 wherein $R^1$ is hydrogen; a saturated 5-, 6- or 7-membered heterocycle containing one or two heteroatoms selected from oxygen, sulfur or nitrogen; indanyl; bicyclo[2.2.1]-2-heptenyl;

bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

10. A compound according to claim 1 wherein $R^4$ is $C_{3-6}$cycloalkyl; $C_{3-6}$cycloalkylaminocarbonyl; or
$C_{1-6}$alkyl substituted with amino or $C_{1-4}$alkylcarbonylamino; or $R^4$ is a radical of formula:

—O—$R^6$ (a-1); or

—NH—$R^7$ (a-2);

wherein $R^6$ is $C_{1-6}$alkyl substituted with carboxyl, $C_{1-4}$alkyloxycarbonyl, amino, mono- or di($C_{1-4}$alkyl)amino, Het$^1$ or aryl;

$R^7$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, Het$^1$ or aryl; or $R^4$ and $R^5$ taken together form a bivalent radical of formula:

—(CH$_2$)$_n$—(b-1);

—CH$_2$—CH$_2$—O—CH$_2$—CH$_2$—(b-2);

—CH$_2$—CH$_2$—N(R$^8$)—CH$_2$—CH$_2$—(b-3); or

—CH$_2$—CH=CH—CH$_2$—(b-4);

wherein
n is 2, 3, 4 or 5;
$R^8$ is hydrogen, $C_{1-6}$alkyl, $C_{1-6}$alkylsulfonyl or p-toluenesulfonyl.

11. A compound according to claim 1 wherein $R^1$ is $C_{1-6}$alkyl, $C_{3-6}$cycloalkyl or $C_{1-10}$alkyl substituted with $C_{3-7}$cycloalkyl and $R^2$ is $C_{1-6}$alkyl.

12. A compound according to claim 1 wherein Y is methylene.

13. A compound according to claim 1 wherein L is hydrogen.

14. A compound according to claim 1 wherein the compound is selected from

1-[[1-[3-(cyclopentyloxy)-4-methoxyphenyl] cyclopropyl]-methyl]-1,3-dihydro-2H-imidazol-2-one;

1-[2-[3-(cyclopentyloxy)-4-methoxyphenyl]-2-methylpropyl]-1,3-dihydro-2H-imidazol-2-one;

1-[2-[3-(cyclopentyloxy)-4-methoxyphenyl]propyl]-1,3-dihydro-2H-imidazol-2-one; and 1-[2-[3-(cyclopropylmethoxy)-4-methoxyphenyl] propyl]-1,3-dihydro-2H-imidazol-2-one, a stereoisomeric form or a pharmaceutically acceptable acid addition salt thereof.

15. A pharmaceutical composition comprising a pharmaceutically acceptable carrier and as active ingredient an amount of a compound as described in claim 1, said amount being effective for treating allergic, atopic and inflammatory diseases.

16. A process of preparing a pharmaceutical composition comprising mixing a therapeutically effective amount of a compound as claimed in claim 1 with a pharmaceutical carrier.

* * * * *

UNITED STATES PATENT AND TRADEMARK OFFICE
CERTIFICATE OF CORRECTION

PATENT NO. : 6,403,805 B1
DATED : June 11, 2002
INVENTOR(S) : Eddy Jean Edgard Freyne et al It is certified that error appears in the above-identified patent and that said Letters Patent is hereby corrected as shown below:

Title page,
Item [54], Title, replace "1,3-Dihydro-1-(Phenylalkyl)-2H-Imidazol-2-One Derivatives" with -- 1,3-Dihydro-1-(Phenylalkyl)-2H-Imidazol-2-One Compounds --

Column 43,
Line 2, replace "$R^4R^5$" with -- $R^4$ and $R^5$ --
Line 33, replace "$C_{1-4}$alkyloxy, $C_{1-4}$alkyloxycarbonyl" with -- $C_{1-4}$alkyloxy, $C_{3-6}$ cycloalkyl, trifluoromethyl, amino, nitro, carboxyl, $C_{1-4}$alkyloxycarbonyl --

Column 44,
Line 47, replace "$R^4R^5$" with -- $R^4$ and $R^5$ --
Line 59, replace "Y is a direct bond," with -- Y is a direct bond --

Column 45,
Line 57, replace "$C_{1-6}$ alkylcarbonylamino" with -- $C_{1-4}$alkylcarbonylamino --

Column 46,
Line 1, replace "$C_{1-6}$ alkylcarbonyl" with -- $C_{1-4}$alkylcarbonyl --

Signed and Sealed this

Twenty-first Day of September, 2004

JON W. DUDAS
*Director of the United States Patent and Trademark Office*